Figure 1A:
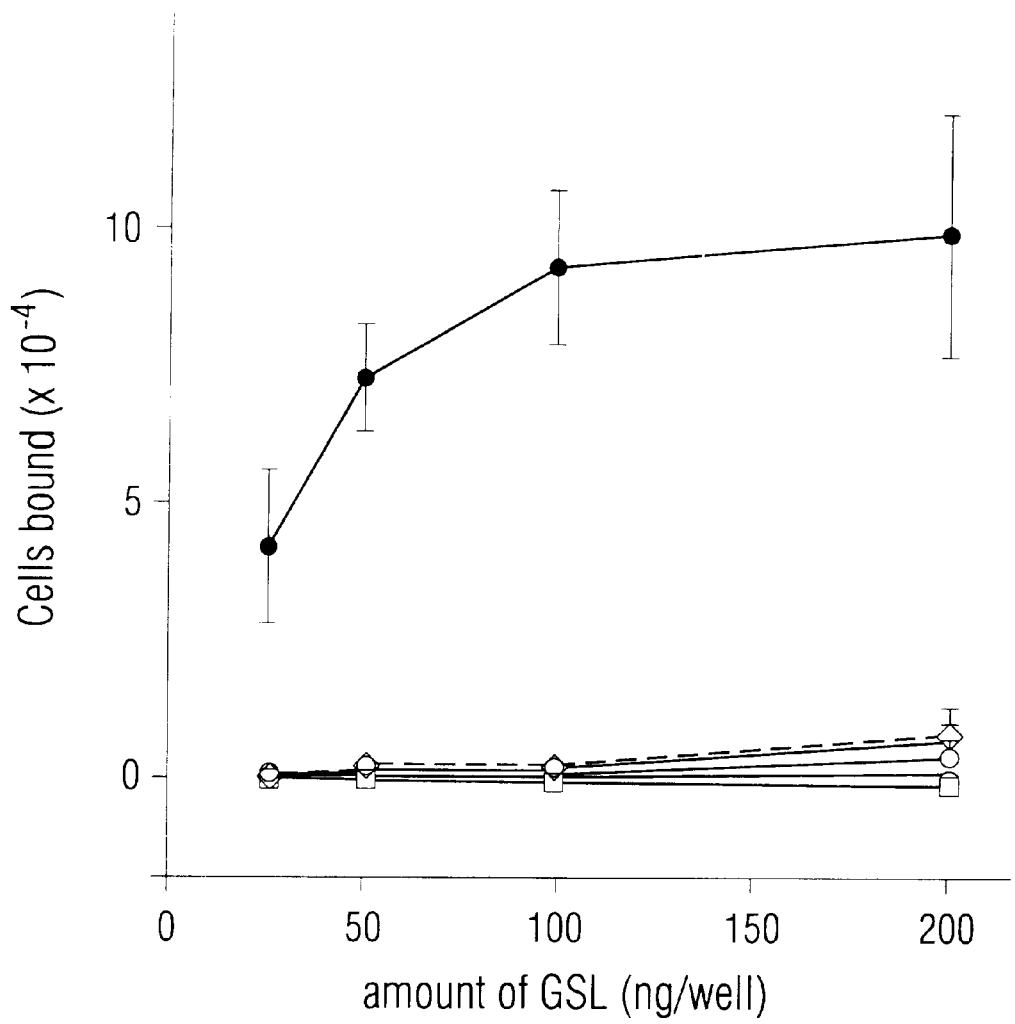

United States Patent [19]
Handa et al.

[11] Patent Number: 6,133,239
[45] Date of Patent: *Oct. 17, 2000

[54] CARBOHYDRATE LIGANDS (MYELOROLLIN) THAT CAUSE E-SELECTIN DEPENDENT CELL ROLLING AND ADHESION UNDER DYNAMIC FLOW SYSTEM

[75] Inventors: Kazuko Handa, Bellevue; Mary Ellen K. Salyan, Silverdale; Mark R. Stroud, Seattle; Sen-itiroh Hakomori, Mercer Island, all of Wash.

[73] Assignees: The Biomembrane Institute, Wash.; Seikagaku Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/688,124

[22] Filed: Jul. 29, 1996

Related U.S. Application Data

[63] Continuation of application No. 08/635,849, Apr. 22, 1996, Pat. No. 5,876,715, which is a continuation-in-part of application No. 08/516,174, Aug. 17, 1995, abandoned.

[51] Int. Cl.$^7$ ............................. A61K 31/70; C07H 15/00
[52] U.S. Cl. ........................... 514/25; 536/4.1; 536/17.2; 536/53; 536/55; 536/55.1; 514/54; 514/62
[58] Field of Search .................................. 536/4.1, 17.2, 536/53, 55, 55.1; 514/25, 54, 62

[56] References Cited

U.S. PATENT DOCUMENTS

| | | | |
|---|---|---|---|
| 4,851,511 | 7/1989 | Hakomori et al. | 530/387.5 |
| 5,011,920 | 4/1991 | Hakomori et al. | 536/53 |
| 5,198,424 | 3/1993 | McEver | 514/13 |
| 5,211,936 | 5/1993 | Brandley et al. | 424/1.73 |
| 5,227,369 | 7/1993 | Rosen et al. | 514/23 |
| 5,268,364 | 12/1993 | Kojima et al. | 514/25 |
| 5,316,913 | 5/1994 | Butcher et al. | 435/7.24 |
| 5,326,752 | 7/1994 | Nashed et al. | 514/25 |
| 5,369,017 | 11/1994 | Wong et al. | 435/68.1 |
| 5,369,096 | 11/1994 | Yamada et al. | 514/61 |
| 5,412,123 | 5/1995 | Rao et al. | 552/209 |
| 5,418,129 | 5/1995 | Nudelman et al. | 435/2 |
| 5,426,178 | 6/1995 | Laine et al. | 536/1.11 |

FOREIGN PATENT DOCUMENTS

| | | |
|---|---|---|
| 0 344 955 | 12/1989 | European Pat. Off. . |
| WO 91/19501 | 12/1991 | WIPO ............... A61K 31/70 |
| WO 91/19502 | 12/1991 | WIPO ............... A61K 31/70 |

OTHER PUBLICATIONS

European Search Report, dated Feb. 12, 1997, for EP 96 11 3074.
Alon et al., 1995, *J. Immunol.*. 154:5356–5366.
Asada et al., 1991, *Biochem.* 30:1561–1571.
Atkins et al., 1974, *Polymer* 15:263–271.
Berg et al., 1991, *J. Biol. Chem.* 266:14869–14872.
Fukada et al., 1979, *J. Biol. Chem.* 254:5458–5465.
Fukada et al., 1984, *J. Biol. Chem.* 259:10925–10935.
Fukushi et al., 1984, *J. Biol. Chem.* 259:10511–10517.
Fukushima et al., 1984, *Cancer Res.* 44:5279–5285.
Handa et al., 1991, *Biochem. Biophys. Res. Comm.* 181:1223–1230.
Handa et al., 1995, *Int. J. Oncol.* 6:773–781.
Ito et al., 1994, *Glycoconj. J.* 11:232–237.
L.A. Lasky, 1995, *Ann. Rev. Biochem.* 64:113–139.
Lawrence et al., 1987, *Blood* 70:1284–1290.
Lawrence et al., 1990, *Blood* 75:227–237.
Lawrence & Springer, 1991, *Cell* 65:859–873.
Lowe et al., 1991, *J. Biol. Chem.* 266:17467–17477.
Macher et al., 1988, *J. Biol. CHem.* 263:10186–10191.
Mulligan et al., 1993, *J. Exp. Med.* 178:623–631.
Muroi et al., 1992, *Blood* 79:713–719.
Niemann et al., 1978, *Biochem. Biophys. Res. Comm.* 81:1286–1293.
Nudelman et al., 1988, *J. Biol. Chem.* 263:13942–13951.
Osanai et al., 1996, *Biochem. Biophys. Res. Comm.* 218:610–615.
Patel et al., 1994, *Biochem.* 33:14815–14824.
Phillips et al., 1990, *Science* 250:1130–1132.
Polley et al., 1991, *PNAs USA* 88:6224–6228.
Rees et al., 1975, *MTP International Rev. of Science*, W.J. Whelan, ed., Butterworths (London), Univ. Park Press (Baltimore) 5:1–42.
Sako et al., 1993, *Cell* 75:1179–1186.
Stroud et al., Apr. 26, 1995, *Biochem. Biophys. Res. Comm.* 209:777–787.
Stroud et al., 1996, *Biochem.* 35:758–769.
Stroud et al., 1996, *Biochem.* 35:770–778.
Takada et al., 1991, *Biochem. Biophys. Res. Comm.* 179:713–719.
Tiemeyer et al., 1991, *PNAS USA* 88:1138–1142.
Tyrrell et al., 1991, *PNAS USA* 88:10372–10376.
A. Varki, 1994, *PNAS USA* 91:7390–7397.
Walz et al., 1990, *Science* 250:1132–1135.
Yang & Hakomori, 1971, *J. Biol. Chem.* 246:1192–1200.

Primary Examiner—Kathleen K. Fonda
Attorney, Agent, or Firm—Pennie & Edmonds LLP

[57] ABSTRACT

An unbranched polylactosamine comprising at least 6 monosaccharides and having terminal α2→3 sialylation and internal α1→3 fucosylation at various N-acetylglucosamine residues except for solely at the penultimate N-acetylglucosamine residue.

22 Claims, 17 Drawing Sheets

CARBOHYDRATE LIGANDS (MYELOROLLIN) THAT CAUSE E-SELECTIN DEPENDENT CELL ROLLING AND ADHESION UNDER DYNAMIC FLOW SYSTEM

This application is a continuation of application Ser. No. 08/635,849, filed Apr. 22, 1996, now U.S. Pat. No. 5,876,715 which is a continuation-in-part of the application Ser. No. 08/516,174, filed Aug. 17, 1995, now abandoned, the entire disclosures of which are incorporated herein by reference.

1. FIELD OF THE INVENTION

The present invention generally relates to compounds having saccharide sequences that cause, under dynamic flow conditions, rolling and adhesion of E-selectin expressing cells. The present invention more particularly relates to the presence of a group of monosialofucogangliosides that cause rolling and adhesion of E-selectin expressing cells. The invention is based on the discovery that novel carbohydrate ligands (called "myelorollin") expressed on leukocytes and leukemic cells mediate E-selectin dependent rolling and adhesion to activated endothelial cells at sites of inflammation under dynamic flow conditions. Myelorollin is a group of unbranched polylactosamine compounds having $\alpha 2 \rightarrow 3$ sialosyl residue at the terminus and $\alpha 1 \rightarrow 3$ fucosyl residues at the internal GlcNAc but not at the penultimate GlcNAc. The invention is also based on the finding that mixtures of different myelorollins show synergism in causing rolling and adhesion of E-selectin expressing cells under dynamic flow conditions. In this specification, unless otherwise indicated, the term "rolling" includes plain rolling, rolling followed by adhesion and adhesion followed by rolling and the term "adhesion" means plain adhesion without any accompaniment of rolling.

2. BACKGROUND OF THE INVENTION

Since 1989, cloning of vascular or platelet adhesive proteins, now termed "selectins," has led to focused attempts to identify carbohydrate epitopes which are expressed on leukocytes (Varki, A., 1994, Proc. Natl. Acad. Sci. U.S.A. 91:7390–7397; Lasky, L. A., 1995, Ann. Rev. Biochem. 64:113–139) and function as targets of selectin-dependent "rolling" and adhesion of leukocytes on activated endothelial cells, followed by transendothelial migration. This mechanism plays a central role in inflammatory responses (Lasky, L. A., 1995, Ann. Rev. Biochem. 64:113–139). Such epitopes are involved in recruitment of the cells to inflammatory sites following infection or wounding. Currently, sialosyl-Le$^x$ (SLe$^x$) is generally believed to be the target epitope of E-selectin binding, based on the following claims: (i) Human leukocytes, leukemic leukocytes, and leukemic cell lines (e.g., HL60 and U937 cells), but not non-human leukocytes, express SLe$^x$. This claim was based on strong reactivities of these types of cells with mAbs believed to be directed to SLe$^x$ (Ito et al., 1994, Glycoconj. J. 11:232–237). These SLe$^x$-expressing cells adhere to activated endothelial cells or platelets which express E- or P-selectin (Phillips et al., 1990, Science 250:1130–1132; Polley et al., 1991, Proc. Natl. Acad. Sci. U.S.A. 88:6224–6228). (ii) Chinese Hamster Ovary (CHO) cells expressing sialosyl type 2 chain do not adhere to E-selectin, whereas transfectants of these cells with fucosyltransferase III cDNA do adhere to E-selectin (Lowe et al., 1991, J. Biol. Chem. 266:17467–17477). (iii) E-selectin-dependent adhesion of SLe$^x$-expressing cells to activated ECs is inhibited by liposomes containing SLe$^x$GSLs, or by oligosaccharides with terminal SLe$^x$ structure (Phillips et al., 1990, Science 250:1130–1132; Polley et al., 1991, Proc. Natl. Acad. Sci. U.S.A. 88:6224–6228; Handa et al., 1991, Biochem. Biophys. Res. Commun. 181:1223–1230).

These observations have encouraged acceptance of the idea that SLe$^x$ is the epitope to which E-selectin binds. E- and P-selectin also bind to SLe$^a$, the positional isomer of SLe$^x$ (Handa et al., 1991, Biochem. Biophys. Res. Commun. 181:1223–1230; Berg et al., 1991, J. Biol. Chem. 266:14869–14872; Takada et al., 1991, Biochem. Biophys. Res. Commun. 179:713–719); however, SLe$^a$ is absent in leukocytes and is not considered to be a physiologic epitope of selectins for hematopoietic cells. There has been no systematic characterization of SLe$^x$-containing gangliosides present in neutrophils and HL60 cells, nor any unambiguous demonstration that SLe$^x$ is the major epitope present in N-linked or O-linked glycoprotein side chains in normal or leukemic leukocytes or cell lines derived therefrom.

It is reported that, in an IgG immune complex model of rat with neutrophil-mediated and E-selectin-dependent lung injury, SLe$^x$ provides protective effects against inflammatory vascular injury (Mulligan et al., 1993, J. Exp. Med. 178:623–631).

However, it is also reported that, from the results of immunostaining by antibodies and of indirect binding assay to E- or P-selectin affixed on plate, of human neutrophil (polymorphonuclear leukocytes; PMN), only human PMN and promyelogenous leukemia HL60 cell expressed SLe$^x$ and other lacto-series epitopes, such as Le$^x$ or Le$^y$, but no other mammalian PMN, such as PMN of baboon, macaque, pig, rabbit, rat, guinea pig and hamster (Ito et al., 1994, Glycoconj. J. 11:232–237). And that the E-selectin ligand saccharide sequences obtained from mouse kidney and murine leukocyte are identified as,

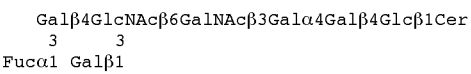

and

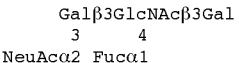

(Osanai et al., 1996, Biochem. Biophys. Res. Commun. 218:610–615).

These reports showed that ligands for selectin of mammals other than human beings are not SLe$^x$. And hitherto certified results on anti-inflammatory effects obtained by using animal models have become questionable.

Further, it is disclosed that, when in vitro, liposomes containing the glycolipid;

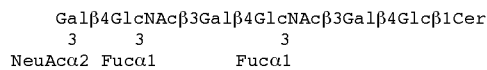

are added to activated endothelial cells and thereto HL60 cells are added, binding of HL60 cells to activated endothelial cells are selectively blocked (WO91/19501 and WO91/19502).

Further, it is reported that glycolipids extracted from leukocytes of patients with chronic myelogenous leukemia was either absorbed to polyvinyl chloride microtiter wells or resolved on TLC plates, screened by binding to COS cells expressing endothelial leukocyte adhesion molecule-1 (ELAM-1) and analyzed structurally, so that detected was the glycolipid below:

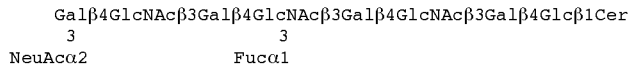

(Proc. Natl. Acad. Sci. U.S.A. 88:1138–1142 [1991]).

Further, Stroud et al. (Biochem. Biophys. Res. Commun. 209: 777–787 [1995]) reported that the following glycolipids,

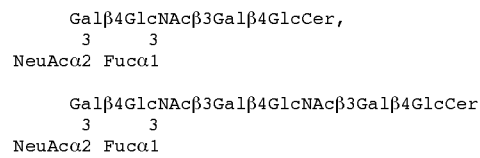

and

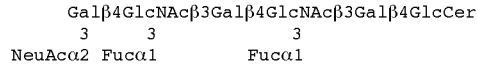

commonly found in solid tumor cells and tissues does not exist in human neutrophils and HL60 cells and that the following glycolipids,

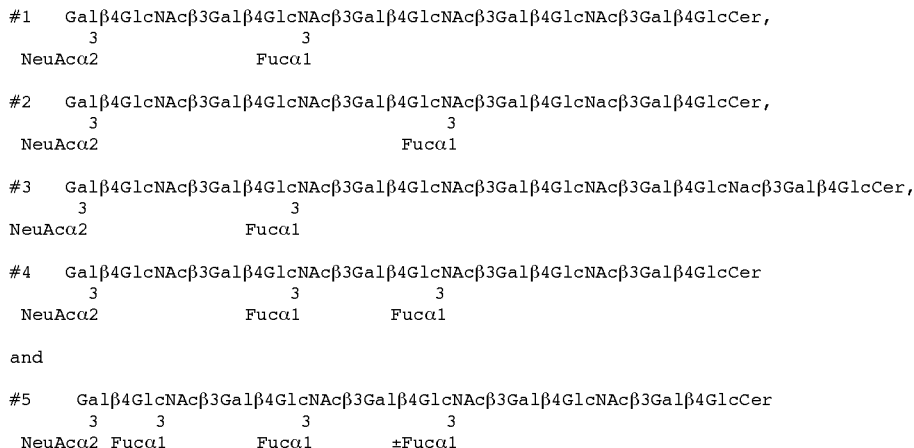

and

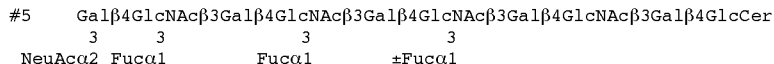

were extracted from human neutrophils and HL60 cells, developed on TLC and placed into contact with E-selectin expressing CHO cells to detect adhesion, which proved that these cells adhered to the glycolipid #4 including very little amount of #5.

On the other hand, since the rolling-type adhesion between the selectins on vascular endothelium and the oligosaccharide ligands of leukocytes participates in the initiation of the inflammatory response, it is expected to protect from influx of leukocytes into the tissue sites of inflammation and localized damage to endothelium by activated neutrophils via an inhibition of leukocyte rolling along endothelium (Lasky, 1995, Ann. Rev. Biochem. 64:113–139).

The currently known E-selectin ligand compounds were selected and proved to be effective under conditions without any shear stress, not taking into consideration the above-mentioned rolling phenomena really occurring in human body. Therefore, these compounds should not be a real E-selectin ligand material. They could control neither E-selectin dependent rolling and adhesion of leukocytes along E-selectin expressing cells, such as endothelium, which is activated in living body nor human inflammation specifically.

It is reported that E-selectin expressing CHO cells tethered under a shear stress of 0.73 dyne/cm$^2$ along the solid phase affixed with SLe$^x$ via egg lecithin phosphatidylcholine (abbreviated as PC). The solid phase used for this experiment was prepared by adding 3 $\mu$l of SLe$^x$ (dissolved at 1 $\mu$g/ml in 20:1 methanol:butanol solution containing 4 $\mu$g/ml PC) to the area having a diameter of 4 mm and drying, whereby, based on the amount added to said solid phase, 15% of SLe$^x$ was affixed via PC to the solid phase (J. Immunol. 154:5356–5366 (1995)). However, as mentioned before, not existing in human neutrophil, SLe$^x$ could not control human inflammation safely and specifically.

A recent report characterized monosialogangliosides of HL60 cells and human neutrophils that bind (or do not bind) to E-selectin under static conditions (Stroud et al., 1995, Biochem. Biophys. Res. Comm. 209:777–787; Stroud et al., 1996, Biochemistry 35:758–769). There was no SLe$^x$ structure, with or without internal fucosylation, having <10-sugar monosaccharide units as poly-LacNAc core structure (Stroud et al., 1996, Biochemistry 35:758–769). All the E-selectin binding fractions had $\alpha2\rightarrow3$ sialosylation at the terminal Gal and two or more $\alpha1 \rightarrow3$ fucosylations at internal GlcNAc other than the penultimate (Stroud et al., 1995, Biochem. Biophys. Res. Comm. 209:777–787; Stroud et al., 1996, Biochemistry 35:770–778). These binding fractions were collectively termed "myeloglycan." There was an extremely minor component of poly-LacNAc having SLe$^x$ terminus with $\alpha1 \rightarrow3$ fucosylation at internal GlcNAc. It was concluded that the major E-selectin binding site in human neutrophils and HL60 cells is myeloglycan type rather than SLe$^x$-containing glycan. None of the myeloglycan or poly-LacNAc SLe$^x$ structures examined showed P-selectin binding (Stroud et al., 1996, Biochemistry 35:758–769; Stroud et al., 1996, Biochemistry 35:770–778).

3. SUMMARY OF THE INVENTION

The present invention generally relates to substantially pure compounds having saccharide sequences that enables rolling and adhesion of E-selectin expressing cells on surfaces coated with said saccharide sequences under dynamic flow conditions. The dynamic flow conditions are those conditions comparable to physiological shear stresses occurring in the human body, such as the shear stresses caused by blood flow. The compounds of the invention preferably have saccharide sequences existing in human neutrophils or other cells similar thereto.

The invention particularly relates to substantially pure myelorollins, myelorollin mimetics as well as compositions comprising such compounds. Myelorollin is embodied by the following group of non-SLe$^x$-containing structures A, B, C, D and X, Y, which are unbranched polylactosamines with terminal α2→3 sialyation and internal fucosylation at various GlcNAc residues except for the penultimate GlcNAc:

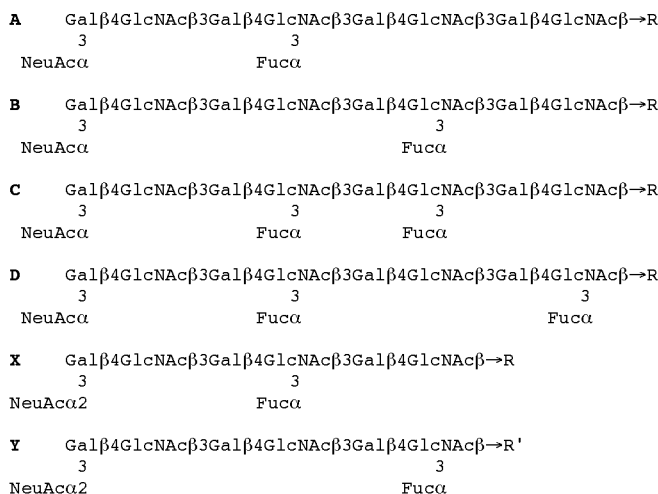

wherein → indicates covalent bond; R and R' each is a H atom, a complex lipid, a simple lipid, an oligosaccharide (R' an oligosaccharide which does not contain any lactosamine residue), a ceramide residue, a substituted or unsubstituted aryl group, an alkyl, alkenyl or hydroxyalkyl group having 1 to 10 carbon atoms, a pharmaceutically active ingredient, a solid carrier, or a covalent compound thereof.

Myelorollin-containing structures, especially that exists in human body as ganglioside, as well as antibodies that block myelorollin caused rolling and adhesion on E-selectin expressing cells, are useful reagents for inhibitive inflammatory responses, particularly chronic conditions such as rheumatoid arthritis, kidney disease, and hepatitis.

A mixture of myelorollin rather than a single molecular species causes stronger rolling and adhesion of E-selectin expressing cells. Therefore, mixtures of myelorollin are particularly useful reagents to inhibit inflammatory responses.

The invention is based on the surprising discovery that E-selectin expressing cells adhered to and rolled on surfaces coated with myelorollin-containing gangliosides.

3.1. ABBREVIATIONS AND DEFINITIONS

The following abbreviations are used throughout this disclosure: BSA, bovine serum albumin; CID, collision-induced dissociation; CHO cells, Chinese hamster ovary cells; EC, endothelial cell; EDTA, ethylenediaminetetra acetic acid; ES-MS, electrospray mass spectrometry, FABMS, fast atom bombardment mass spectrometry; Fr., fraction(s); GSL, glycosphingolipid; Ig, immunoglobulin; IHW, isopropanol/hexane/water; mAb, monoclonal antibody; MFI, mean fluorescence intensity; NMR, nuclear magnetic resonance; PLA, polylactosamine; PBS, phosphate-buffered saline; Sdiy$^2$ or SLe$^x$-Le$^x$, sialosyl Le$^x$-Le$^x$; SLe$^x$, sialosyl-Le$^x$; SLe$^a$, sialosyl-Le $^a$, Str., structure (s); TLC, thin layer chromatography. Glycolipids are abbreviated according to the recommendations of the IUPAC-IUB Commission on Biochemical Nomenclature (Lipids 12:455–463, 1977); however, the suffix -OseCer is shortened to -Cer. In particular, sialosyl-Le$^x$ and sialosylLe$^x$-Le$^x$ have the following structures:

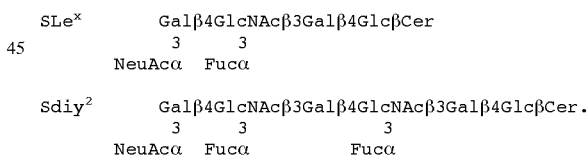

As illustrated in the formulas above, the number "1" to show the glycoside-OH position in saccharide and the arrow to show the bond to adjacent saccharide is, unless otherwise indicated, omitted for abbreviation purpose in this specification.

4. BRIEF DESCRIPTION OF THE DRAWINGS

FIG. 1A. Adhesion of E-selectin expressing CHO cells to wells of 96-well plates coated with various quantities of poly-LacNAc gangliosides under static conditions. Each point represents mean experimental minus control value of triplicate experiments. The symbol "●" represents SLe$^x$-Le$^x$. The other symbols represent Fr. 9, 10-1, 10-2, 12-2.

Figure 1B:
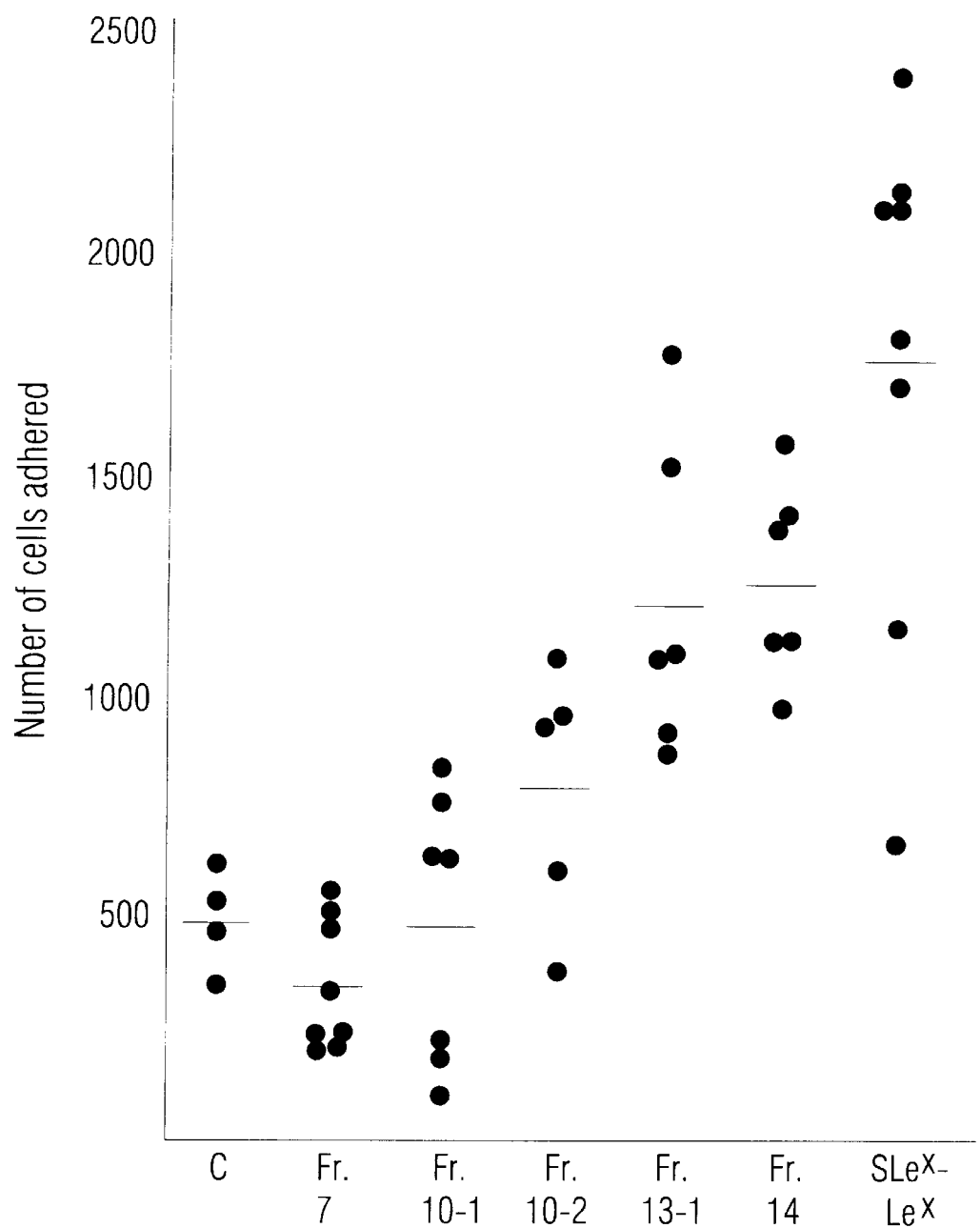

FIG. 1B. Adhesion of E-selectin expressing CHO cells to polystyrene beads (1 μm diameter) coated with various poly-LacNAc gangliosides under static conditions. Each point represents the result of one experiment. Horizontal lines indicate arithmetic means.

FIGS. 2A–2E. Rolling and adhesion of E-selectin expressing CHO cells to polystyrene beads coated with various gangliosides (GSL) under dynamic flow conditions. Gangliosides were quantitatively adsorbed on beads affixed to glass microscope slides as described in the Materials & Methods section. The polystyrene beads affixed on glass plates are resistant to dynamic flow. Slides were blocked by incubating in PBS with 2% BSA at room temp for 1 hr, and assembled in a parallel-plate laminar-flow chamber. E-selectin expressing CHO cells were freshly harvested and suspended in RPMI medium ($1 \times 10^5$ cells/mL). The cell suspensions were placed in an infusion pump connected to the flow chamber, and infused into the assembly at various laminar flow rates. Cell movements were observed under phase-contrast microscope and recorded by videocassette recorder. Numbers of rolling cells (o), and numbers of total rolling and adhesion cells (●), found in at least 10 microscope fields, at four or five different shear stresses (dyne/$cm^2$; see abscissa), were plotted. Numbers of circles greater than 4 are simply represented as 4 on these figures.

Figure 2A:
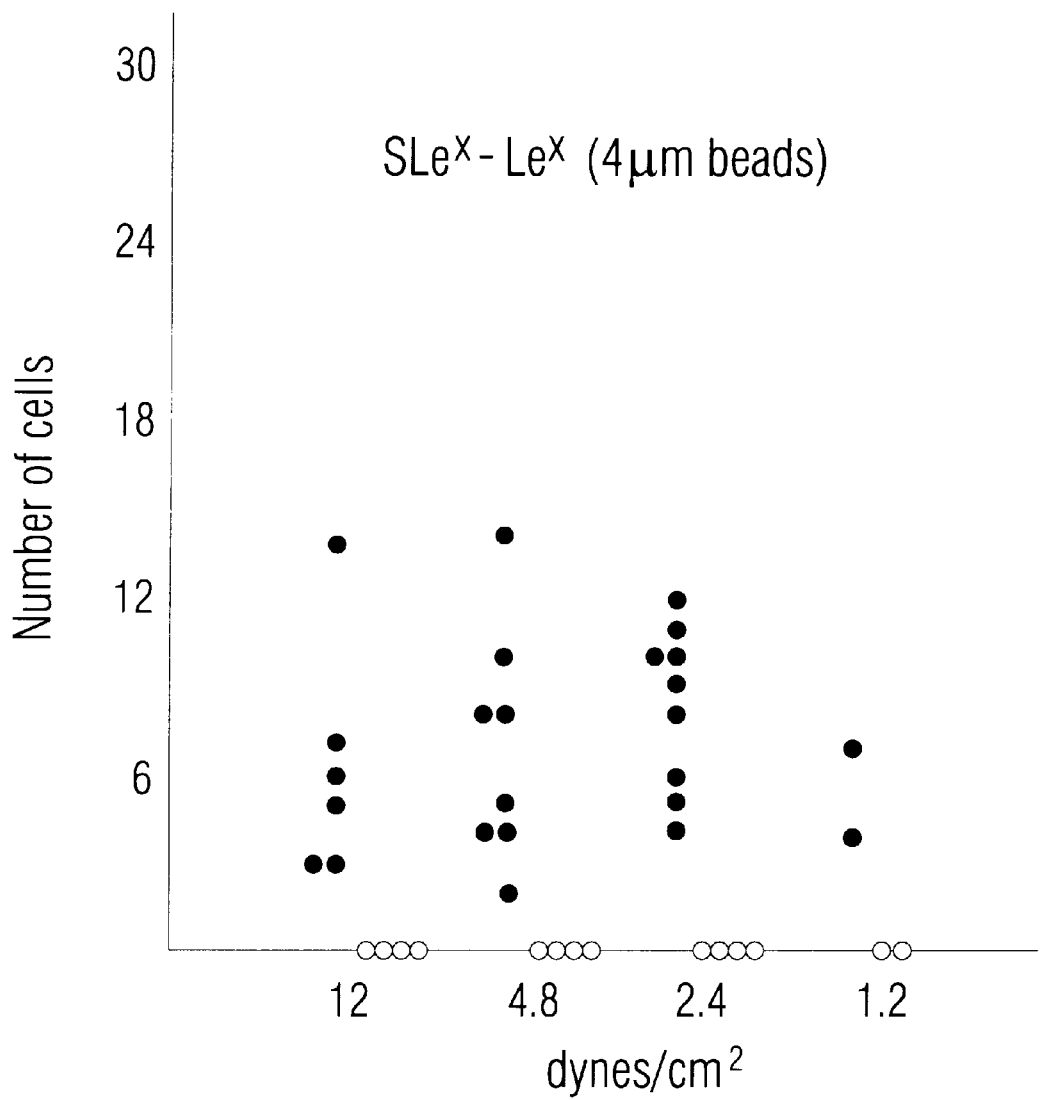

FIG. 2A. Rolling/adhesion of cells on 4 μm beads coated with $SLe^x$-$Le^x$.

Figure 2B:
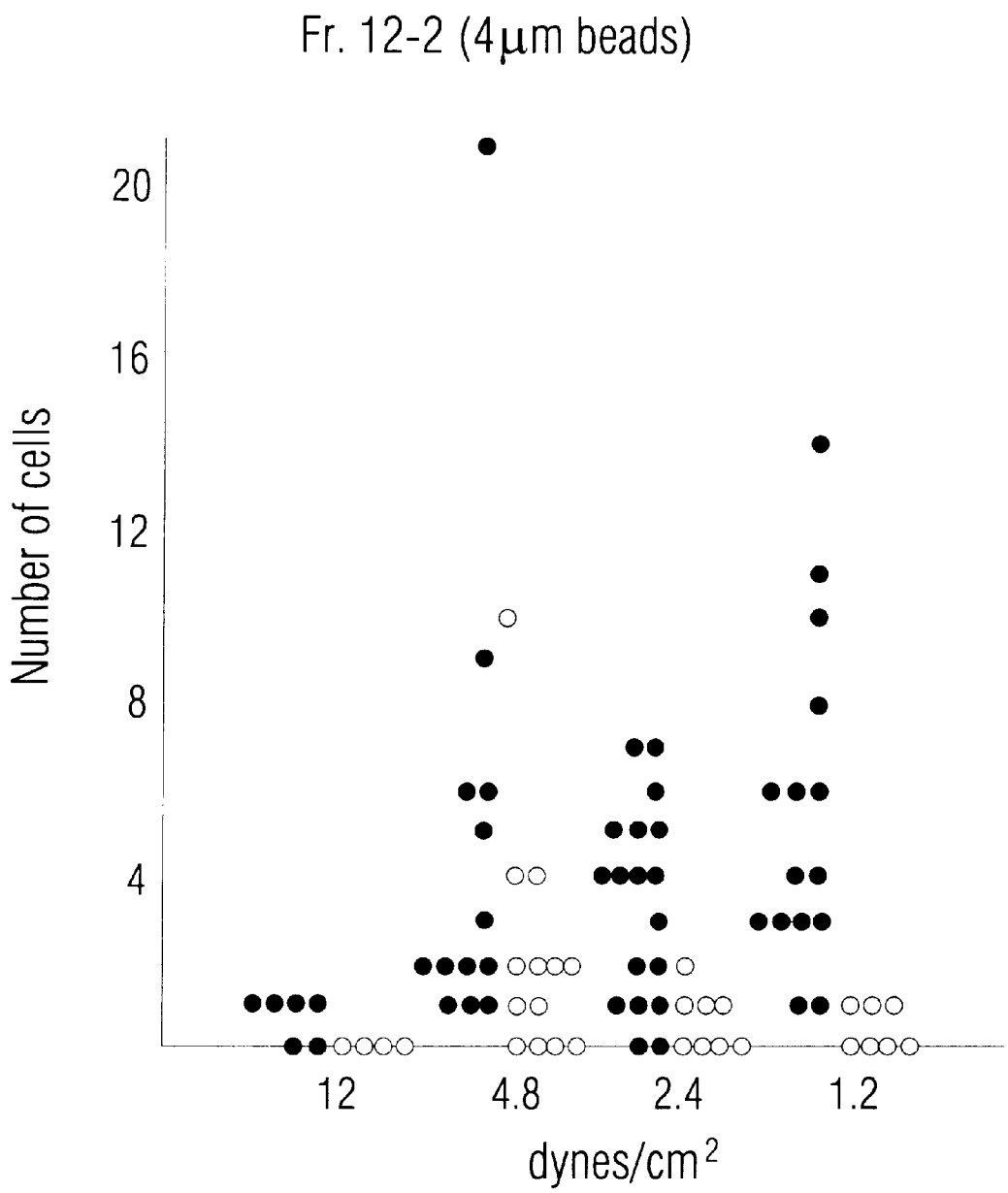

FIG. 2B. Rolling/adhesion of cells on 4 μm beads coated with Fr. 12-2.

Figure 2C:
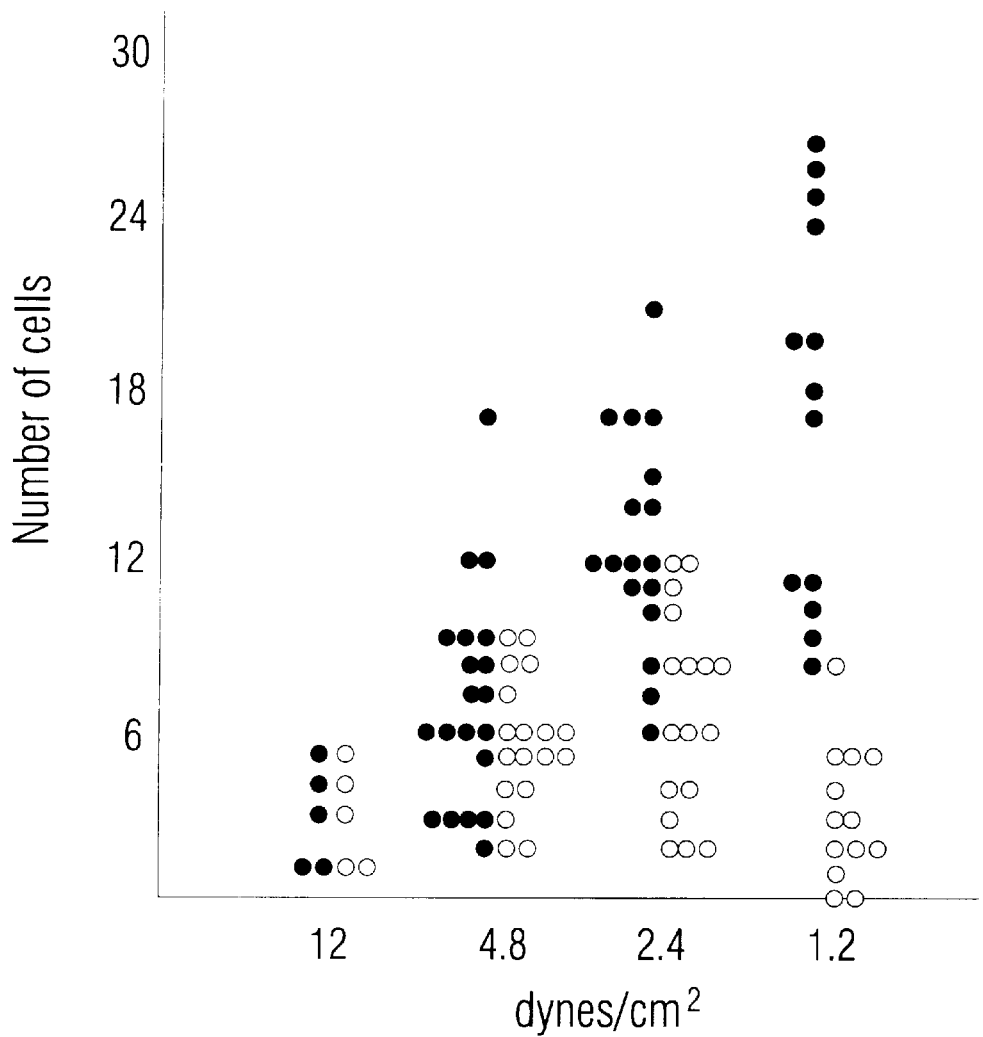

FIG. 2C. Rolling/adhesion of cells on 4 μm beads coated with Fr. 13-1.

Figure 2D:
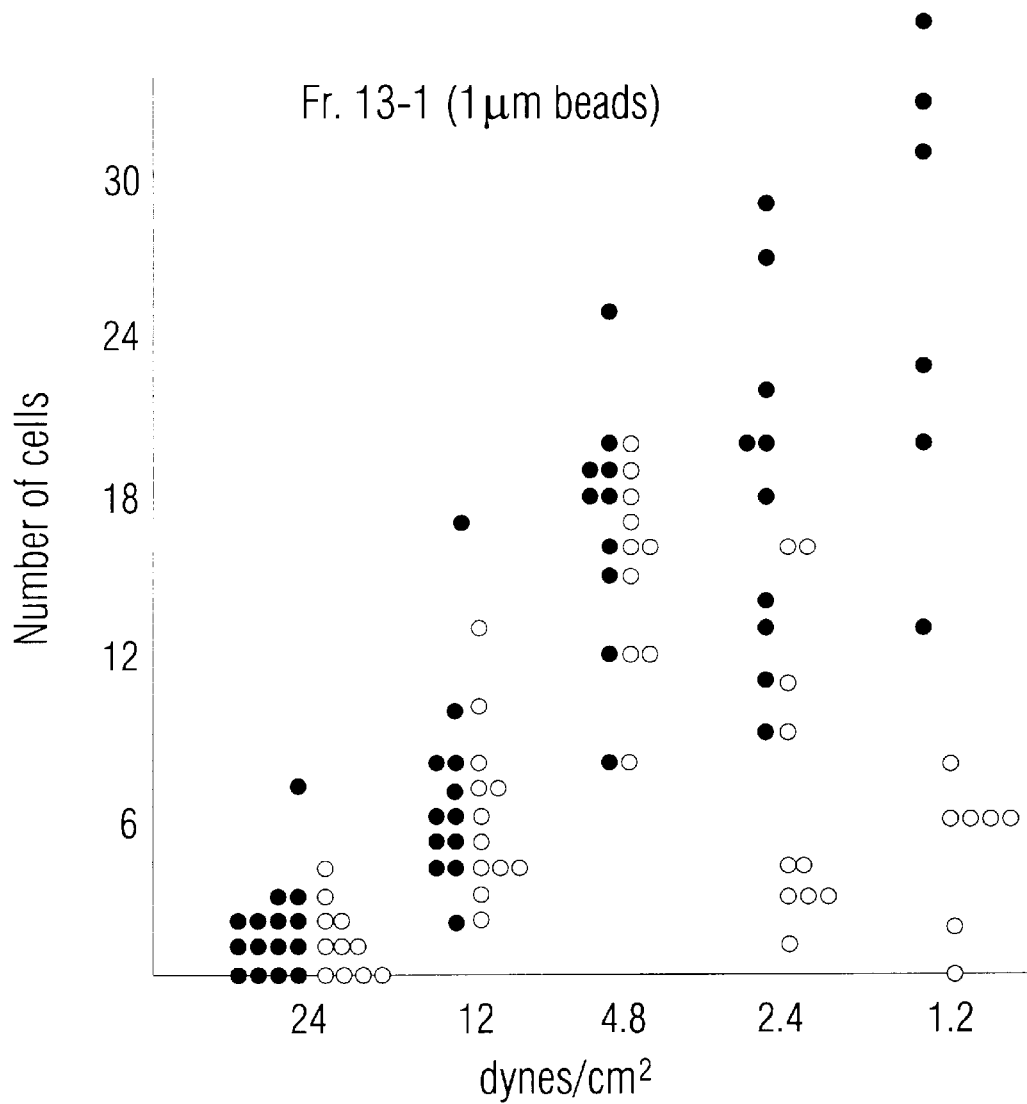

FIG. 2D. Rolling/adhesion of cells on 1 μm beads coated with Fr. 13-1.

Figure 2E:
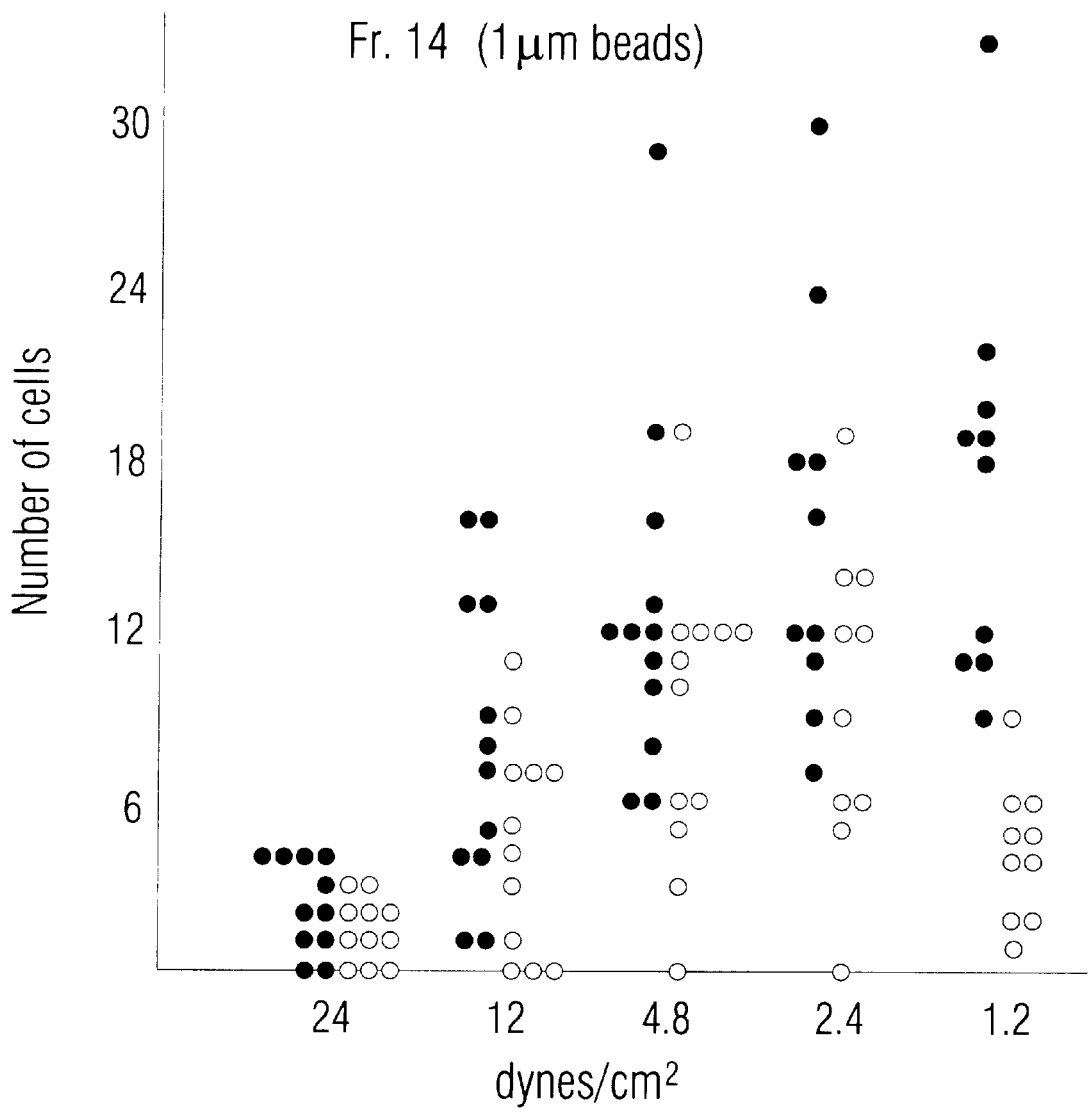

FIG. 2E. Rolling/adhesion of cells on 1 μm beads coated with Fr. 14.

Figure 3A:
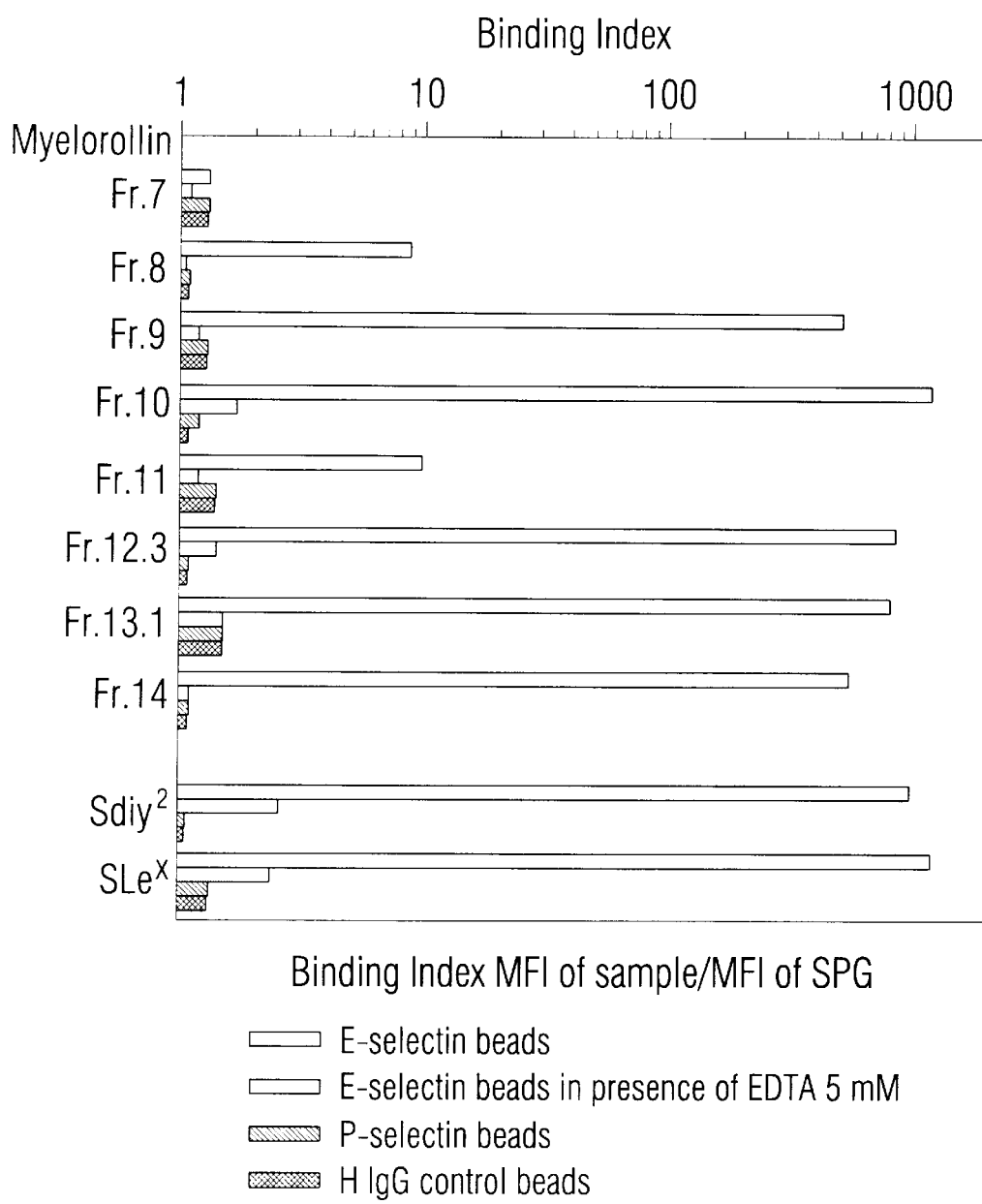

FIG. 3A. Adhesion of E-selectin coated beads to beads coated with various gangliosides under static conditions. Open columns, E-selectin coated beads; lighter shaded columns, E-selectin coated beads in the presence of 5 mM EDTA; darker shaded columns, P-selectin coated beads; and solid columns, human IgG coated beads.

Figure 3B:
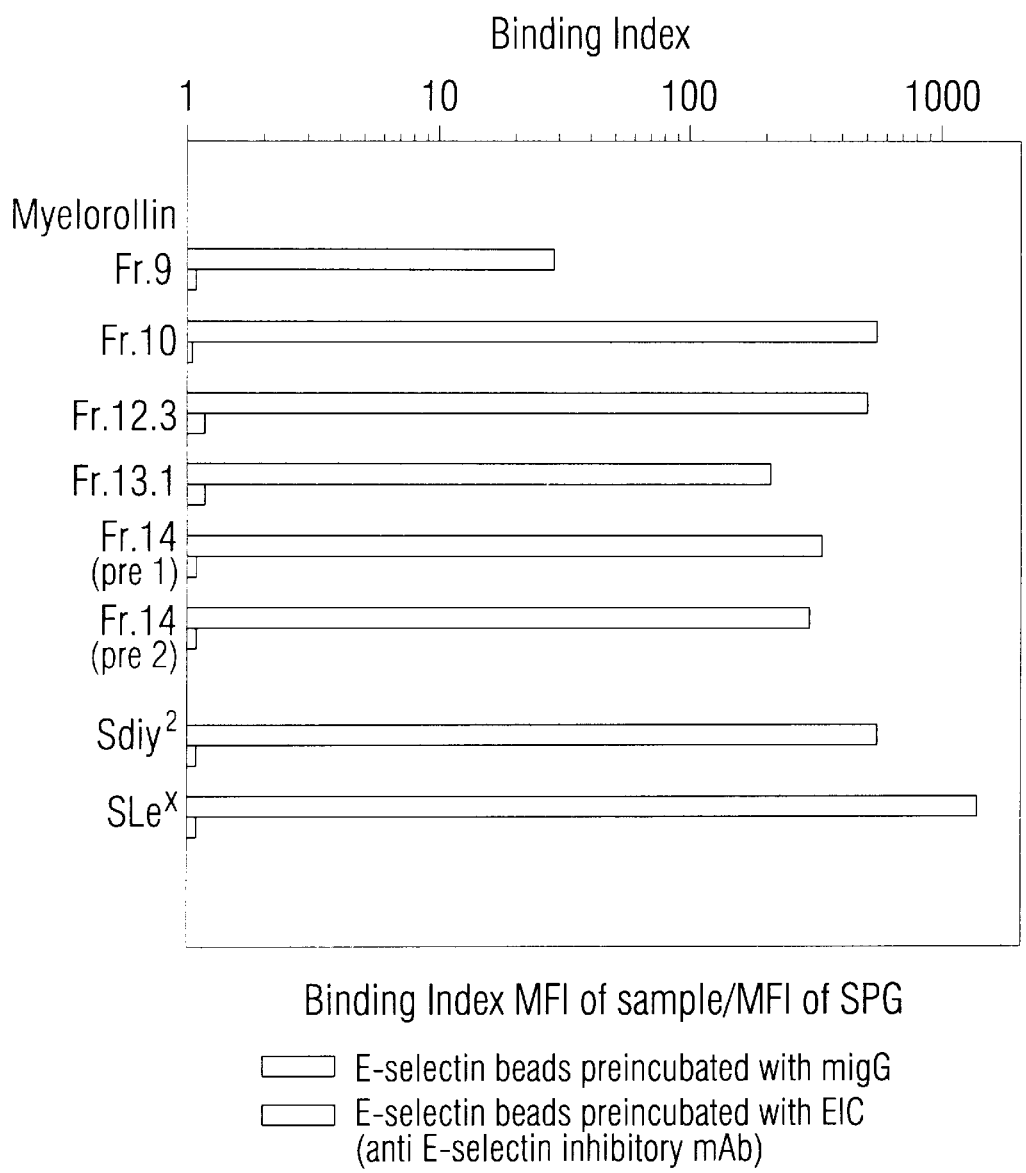

FIG. 3B. Inhibitory effect of anti-E-selectin antibody on E-selectin coated beads binding to beads coated with various myelorollin fractions. Open columns, E-selectin coated beads preincubated with control mouse IgG; and solid columns, E-selectin coated beads preincubated with mAb E1C.

Figure 4A:
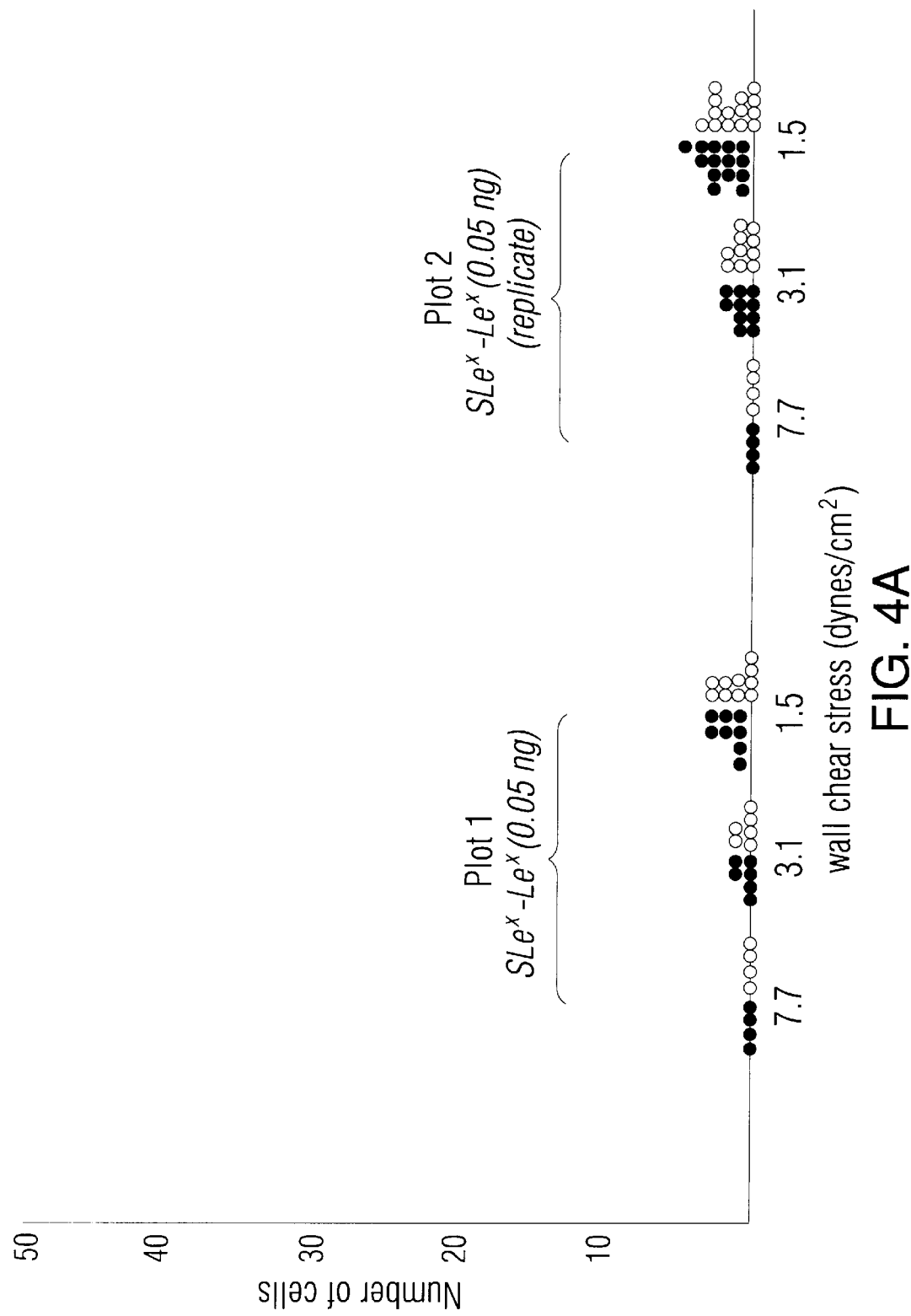
Figure 4B:
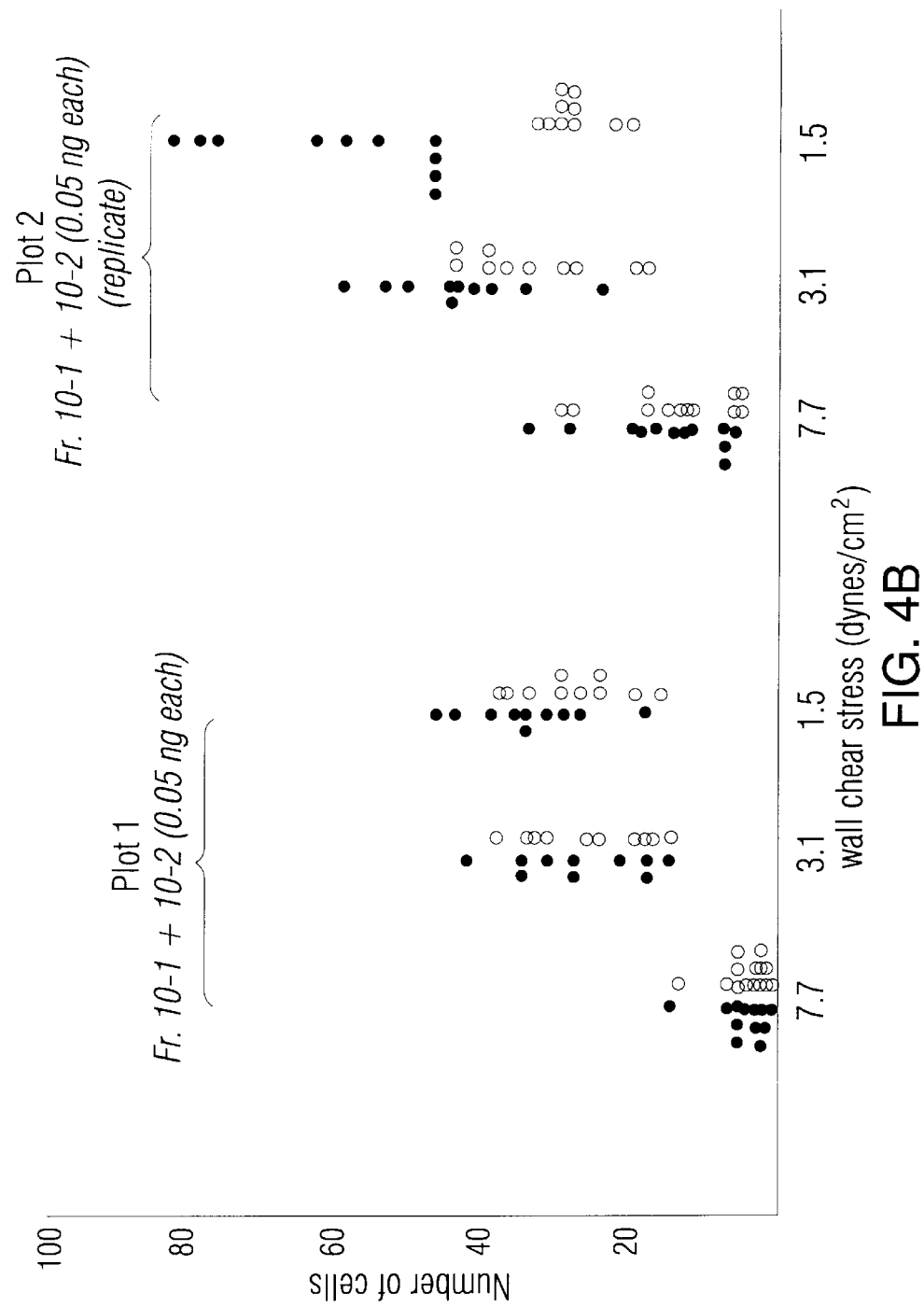
Figure 4C:
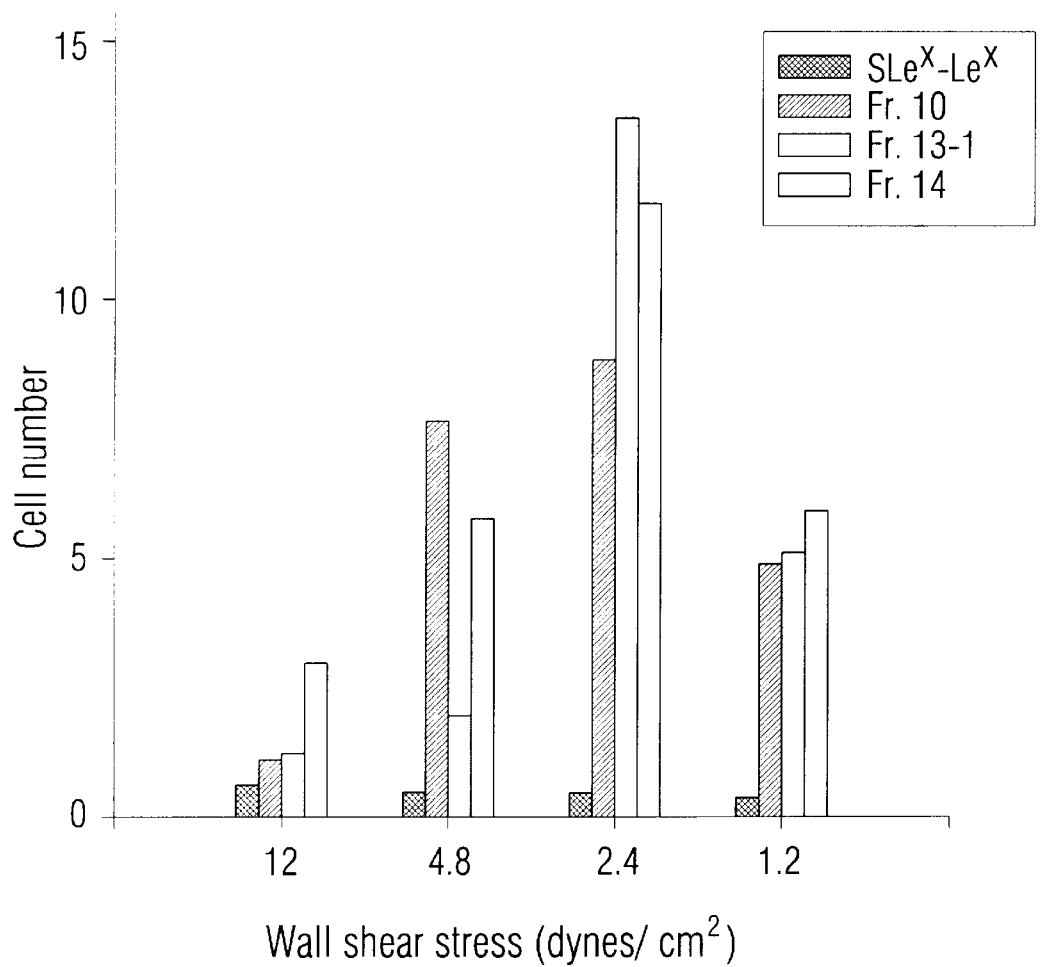

FIGS. 4A–4C. Rolling and adhesion of E-selectin expressing CHO cells on beads coated with very low quantities of $SLe^x$-$Le^x$ or Fraction 10-1 plus Fraction 10-2 under dynamic flow conditions. FIG. 4A. Plot 1. Total rolling and adhesion (●) and rolling (o) of E-selectin expressing CHO cells on beads coated with 0.05 ng of $SLe^x$-$Le^x$ at shear stresses of 7.7, 3.1, and 1.5 dynes/$cm^2$. Plot 2. Replicate experiment, same conditions as plot 1. FIG. 4B. Plot 1. Total rolling and adhesion (●) and rolling (o) of E-selectin expressing CHO cells on beads coated with a mixture of 0.05 ng each of Fr. 10-1 and 10-2 (note: this gives the same molarity as 0.05 ng of $SLe^x$-$Le^x$, because molecular weight of $SLe^x$-$Le^x$ is twice that of Fr. 10-1 or 10-2). Same shear stresses as in FIG. 4A. Plot 2. Replicate experiment, same conditions as plot 1. FIG. 4C. Rolling of E-selectin expressing CHO cells under dynamic flow conditions. Mean value of rolling cell number on beads (diameter 4 μm) coated with various gangliosides (100 ng each) at different shear stresses in dynamic flow system. Ordinate: number of rolling cells (note: includes adherent cells). Abscissa: wall shear stress (dynes/$cm^2$). In each shear stress group, the columns from left to right with respect to the material used to coat the beads, are: $SLe^x$-$Le^x$; Fr. 10 (mixture of Fr. 10-1 and 10-2); Fr. 13-1; and Fr. 14.

Figure 5A:
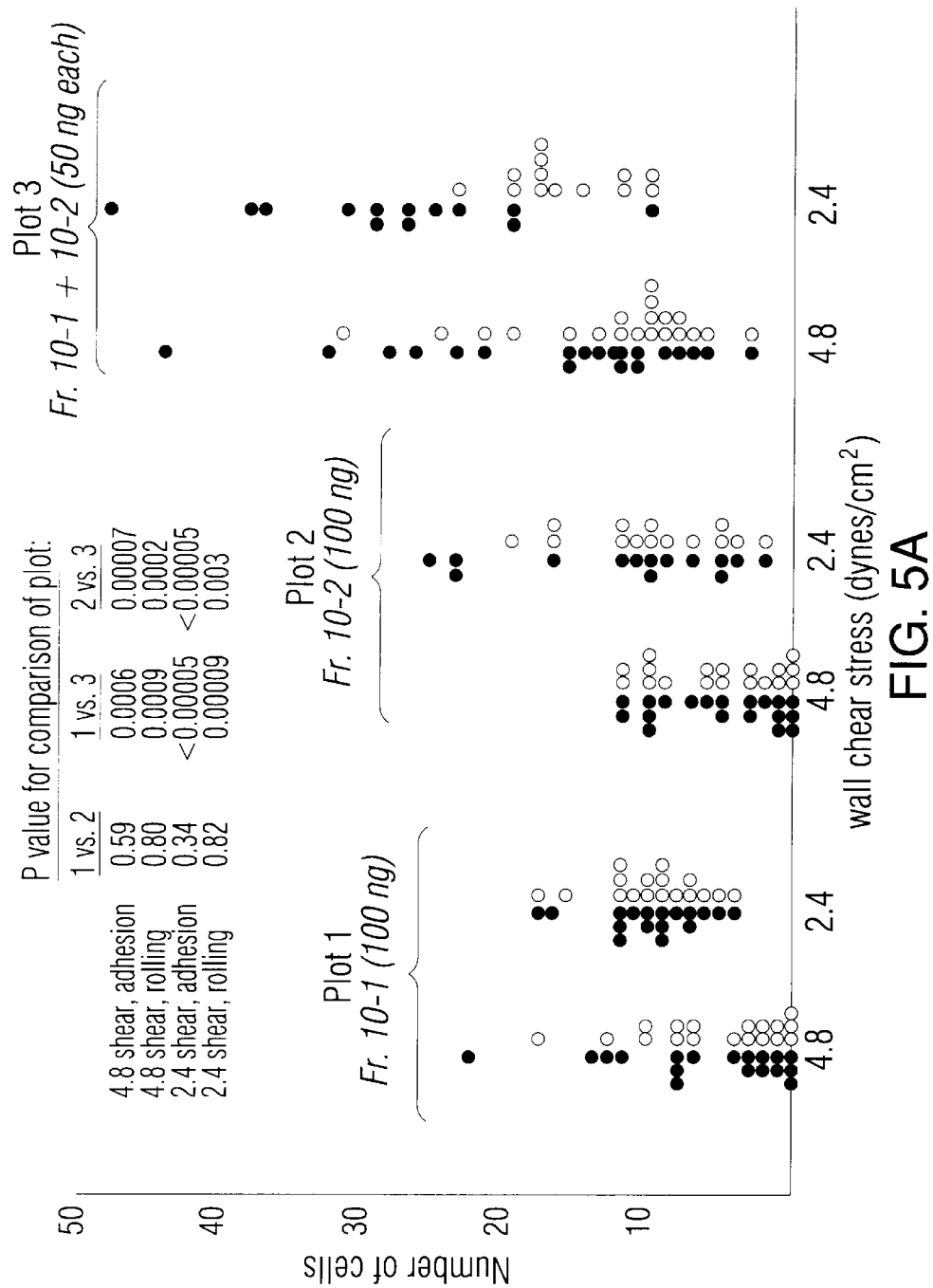
Figure 5B:
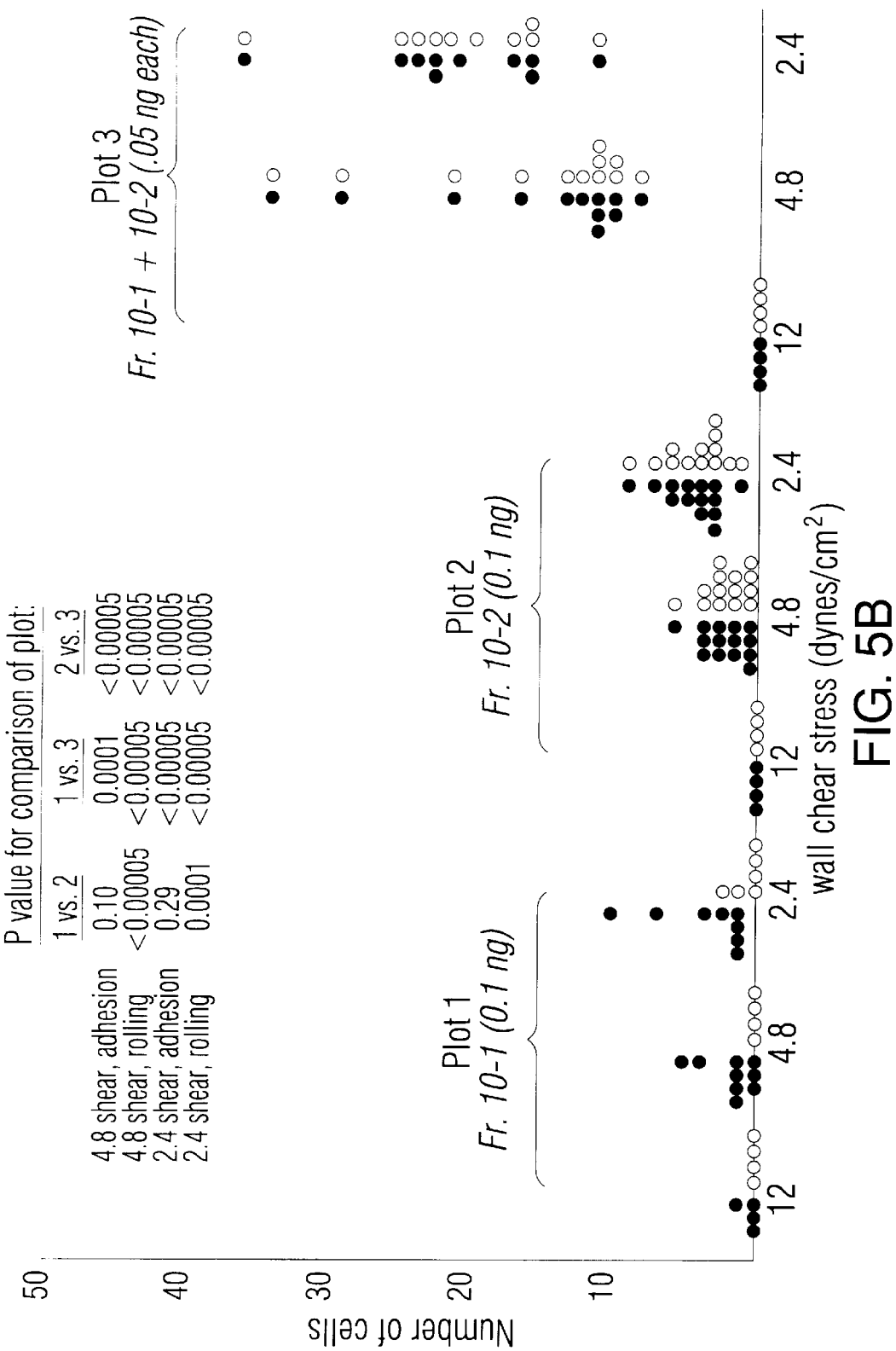

FIGS. 5A and 5B. Rolling and adhesion of E-selectin expressing CHO cells on beads coated with Fr. 10-1, Fr. 10-2 or a mixture of 10-1 and 10-2 under dynamic flow conditions.

FIG. 5A. Total rolling and adhesion (●) and rolling (o) of E-selectin expressing CHO cells on beads coated with: 100 ng of Fr. 10-1 (Plot 1); 100 ng of Fr. 10-2 (Plot 2); and a mixture of 50 ng each of Fr. 10-1 and 10-2 (Plot 3). Gangliosides were adsorbed on 1 μm beads. Values for shear stresses of 2.4 and 4.8 dynes/$cm^2$ are shown. Statistical significance of differences between various subsets of data were evaluated by unpaired Student's t-test, and P values are summarized in the insert table. FIG. 5B. Total rolling and adhesion (●) and rolling (o) of E-selectin expressing CHO cells on beads coated with: 0.1 ng of Fr. 10-1 (Plot 1); 0.1 ng of Fr. 10-2 (Plot 2); and a mixture of 0.05 ng each of Fr. 10-1 and 10-2 (Plot 3). Gangliosides were adsorbed on 1 μm beads. Three different shear stress values are shown. Rolling/adhesion occurred even at this low ganglioside concentration. Number of rolling and adhered cells was greatest for the mixture of gangliosides (Plot 3). P values are summarized in inset table, as in FIG. 5A.

FIGS. 6A–6D. Adhesion and rolling followed by adhesion of E-selectin expressing CHO cells to beads coated with various gangliosides under dynamic flow conditions.

Figure 7:
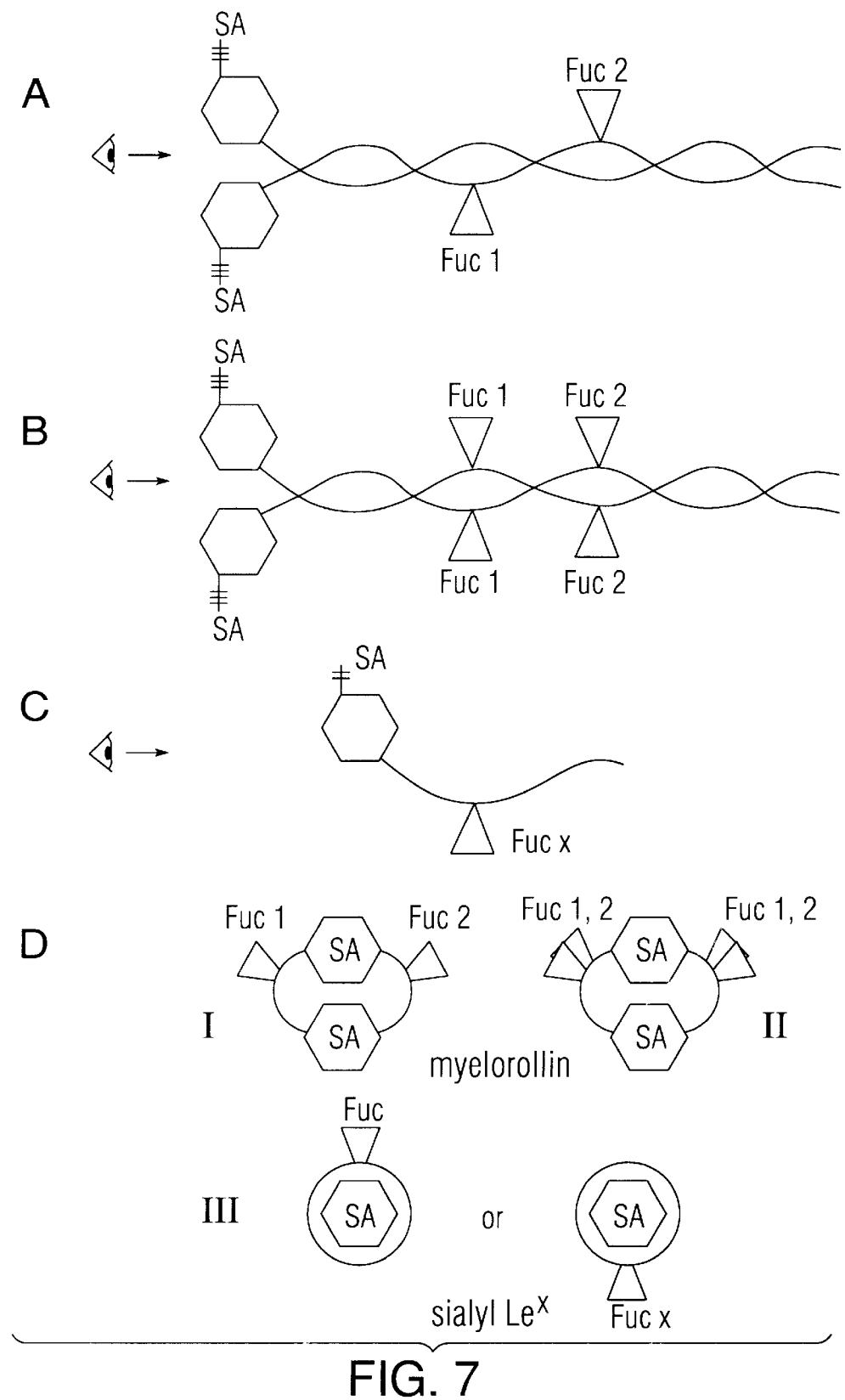

FIG. 7. Possible spatial arrangements of sialosyl residues (SA) and fucosyl residues at the internal GlcNAc of different positions (Fuc1 and Fuc2) along the polylactosamine chain. Panel A: Possible configuration of double helical structure of monofucosylgangliosides having Fuc1 of Fuc2 at different positions (e.g., Str. 4 and 5 or Str. 9 and 10). When this structure is viewed from the terminal end where SA are present, the spatial arrangement of SA and Fuc1, Fuc2 can be seen as shown in I of Panel D. Panel B: Possible configuration of double helical structure of difucosylgangliosides having Fuc1 and Fuc2 at different positions but on the same polylactosamine chain (e.g., Str. 7, Str. 11). When the structure is viewed from the terminal end where SA are present the spatial arrangement of SA and Fuc 1 and Fuc 2 can be seen as shown as in II of Panel D. Panel C: $SLe^x$ structure where Fuc is present at the penultimate GlcNAc (Fuc x); the positional relationship between SA and Fuc x is seen as shown in III of Panel D. Panel D: End views of the gangliosides shown in Panels A–C.

5. DETAILED DESCRIPTION OF THE INVENTION

The present invention provides substantially pure myelorollins, mimetics and compositions thereof. The invention also provides methods of using myelorollins, mimetics and compositions thereof and anti-myelorollin antibodies to inhibit cellular interactions that underlying various diseases. Myelorollins may be isolated from animal cells. Myelorollins, and mimetics may be artificially synthesized. A myelorollin has the ability, when coated on surfaces, to cause rolling, adhesion and streaming of E-selectin expressing cells on such surfaces under dynamic flow conditions.

The myelorollins and mimetics of the invention should be selected by an appropriate procedure. It includes the V procedure comprising affixing probe material, such as gangliosides expressed by human neutrophils or other cells similar thereto, to a solid phase, adding thereto under a shear stress attainable in human body E-selectin expressing cells, such as E-selectin expressing CHO cells, observing, for each time unit, rolling, adhesion and streaming of said cells on said solid phase and consequently selecting materials causing rolling. A shear stress attainable in human body means preferably a shear stress to be caused by human blood flow, in the preferable range of 0.8 to 12 dyne/cm$^{2\cdot}$ The myelorollin or mimetic may be adhered on polystyrene beads affixed to a glass slide which are then placed in a parallel laminar-flow chamber assembly, allowing determination of rolling and adhesion of E-selectin expressing cells under dynamic flow conditions with defined shear stress. The apparatus used may be similar to that described by Lawrence et al., 1990, Blood 75:227.

According to the invention, a myelorollin may have the following structure, which encompasses a group of unbranched polylactosamines consisting of at least 6 monosaccharides (three lactosamine repeating units are shown) and having terminal α2→3 sialylation and internal α1→3 fucosylation at various N-acetylglucosamine residues except for solely at the penultimate N-acetylglucosamine residue:

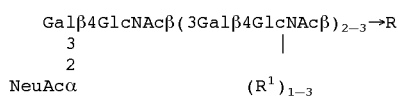

wherein each $R_1$ is independently selected from among —OH and α1→3 fucose ($C_6H_{12}O_5$), provided that at least one $R_1$ is α1→3 fucose.

Embodiments of myelorollin include compounds having the following structures:

wherein → indicates covalent bond; R and R' each is a H atom, a complex lipid, a simple lipid, an oligosaccharide (except R' which does not contain any lactosamine residue), a ceramide residue, a substituted or unsubstituted aryl group, an alkyl, alkenyl or hydroxyalkyl group having 1 to 10 carbon atoms, a pharmaceutically active ingredient, a solid carrier, or a covalent compound thereof.

The groups R and R' may be covalently bound to GlcNAc at the reducing terminus of the formulas via an appropriate spacer, such as diamine, aminoalcohol, amino acid, peptide. As substituents for the aryl group, illustrated are alkyl, alkenyl and alkynyl groups having 1 to 6 carbon atoms, halogen atoms, hydroxyl group, nitro group and carboxyl group. Among complex lipids and simple lipids, ceramide is the most preferred and naturally occurring lipid carrier of myelorollins. Glycerolipids include diacylglycerol and the like neutral lipids. Chain length and unsaturation degree of the acyl group in those lipids are not particularly limited.

The pharmaceutically active ingredients that may form R or R' include, but are not limited to, non-steroid anti-inflammatory drugs: salicylic acid derivatives such as aspirin; aryl acetic acid derivatives such as indomethacin; propionic acid derivatives such as ibuprofen; pyrazolone derivatives such as phenylbutazone; oxicam derivatives such as piroxicam; and epirizol and the like.

The invention also provides myelorollin mimetics which have the following structure, which encompasses a group of unbranched polylactosamines consisting of at least 6 monosaccharides and having terminal α2→3 sialylation and internal α1→3 fucosylation at various N-acetylglucosamine residues except for solely at the penultimate N-acetylglucosamine residue:

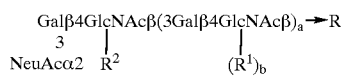

wherein $R_1$ is a α1→3 fucose, $R_2$ is either —OH or fucose, a is an integer of from 2 to 6, b is an integer of from 1 to 6.

Embodiments of myelorollin mimetics include those having the following structures:

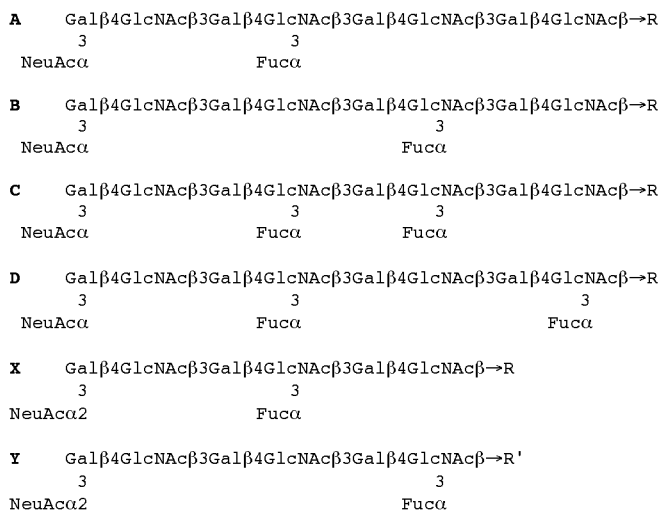

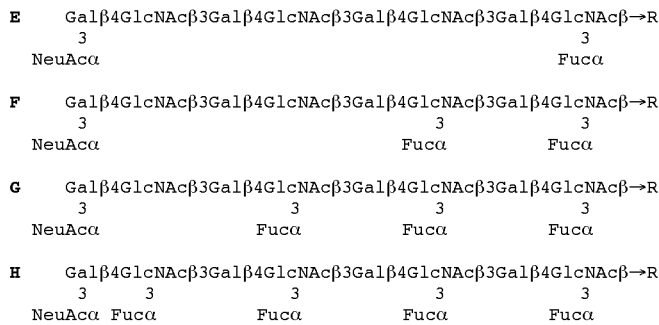

wherein → indicates covalent bond; R is the same as that for the myelorollins described above.

The structures of myelorollin mimetics are distinct from those of myelorollins (e.g., A, B, C, D and X, Y) and may be further defined in terms of possible spatial arrangements of sialosyl residues (SA) and fucosyl residues at the internal GlcNAc of different positions (Fuc1 and Fuc2) along the polylactosamine chain. Poly-N-acetyllactosamine chain ([3Galβ1→4GlcNAcβ1→]$_n$) is known to have a helical structure (Niemann et al., 1978, Biochem. Biophys. Res. Commun. 81:1286–1293; Rees, D. A., 1975, MTP International Review of Science 5:1–42, ed. Whelan, W., Butterworths (London) University Park Press (Baltimore); Atkins et al., 1974, Polymer 15:263–271). Mimetics of myelorollin A, B, C, D and X, Y may be constructed based on spatial configuration, i.e., location of sialic acid and different sites of fucosyl residue. The orientation of fucosyl residue and its relationship with sialic acid position is of primary importance (see FIG. 7).

Myelorollins can be prepared from a large scale culture of HL60 cells or U937 cells as described below. Myelorollins and mimetics can by synthesized in large quantities by polymerization of N-acetyllactosamine followed by α2→3 sialylation and α1→3 fucosylation by sialosyltransferase and fucosyltransferase, respectively.

Specifically, a myelorollin derivative can be obtained by reacting (a) unbranched polylactosamine having α2→3 sialosyl residue at the non-reducing terminus and α1→3 fucosyl residues at the internal GlcNAc but not solely at the penultimate GlcNAc directly or via spacer with (b) a substituted or unsubstituted aryl halide, an alkyl, alkenyl or hydroxyalkyl halide having 1 to 10 carbon atoms, a complex lipid, a simple lipid, an oligosaccharide, a ceramide, a pharmaceutically active ingredient, a solid carrier or a covalent compound thereof using known method, such as glycosylation of the saccharide residue at the reducing terminal.

The present invention also provides a method of inhibiting cell interactions comprising exposing a first cell, such as human neutrophils or leukocytes, that expresses a ligand that causes rolling and adhesion dependent on E-selectin expressed on a second cell, such as endothelial cells and other E-selectin expressing cells, to an E-selectin-dependent rolling and adhesion inhibiting amount of at least one unbranched polylactosamine comprising at least 6 monosaccharides and having terminal α2→3 sialylation and internal α1→3 fucosylation at various N-acetylglucosamine residues except for solely at the penultimate N-acetylglucosamine residue.

Further, the present invention provides a method of inhibiting cell interactions comprising exposing a first cell, such as human neutrophils or leukocytes, that expresses a ligand that causes rolling and adhesion dependent on E-selectin expressed on a second cell, such as endothelial cells and other E-selectin expressing cells, to an E-selectin-dependent rolling and adhesion inhibiting amount of an antibody that binds to an unbranched polylactosamine comprising at least 6 monosaccharides and having terminal α2→3 sialylation and internal α1→3 fucosylation at various N-acetylglucosamine residues except for solely at the penultimate N-acetylglucosamine residue, wherein said antibody is further characterized by inhibiting adhesion of said first and second cells under dynamic flow conditions in vitro.

Myelorollin Preparation from HL60 Cells

HL60 cells. HL60 cells were obtained originally from American Type Culture Collection (ATCC) and grown in RPMI supplemented with 10% FCS. Cells were maintained in 5% $CO_2$ at 37° C., expanded for two cycles in roller bottles to collect large amounts of cells, and harvested by centrifugation. HL60 cells cultured in this manner showed a level of E-selectin binding activity similar to that of cells cultured continuously in a $CO_2$ incubator, i.e., large-scale culture in roller bottles in this way did not cause significant loss of E-selectin binding activity. Altogether, 1200 mL of packed HL60 cells were divided into about 400 mL packed aliquots, each of which was extracted as described in the following section.

Glycolipid extraction. Approximately 100 mL of packed human neutrophils or 400 mL of packed HL60 cells were extracted by homogenization in a Waring blender with 10 volumes of the lower phase of IHW (55:25:20). The extract was filtered through a Whatman #1 filter and the residue re-extracted as above. The extraction/filtration procedure was repeated once more and the combined filtrates were concentrated under reduced pressure at 40° C. using a Brinkmann rotary evaporator. The concentrated extract was subjected to Folch partitioning by dissolving the residue in 3 L of chloroform/methanol (C/M; 2:1) containing 500 mL of water. After vigorous shaking the extract was allowed to separate until two translucent phases appeared (about 8 hr). The upper phase was removed and the lower phase re-extracted by the addition of C/M/1% KCl (1:10:10) to the original volume. The liquid-extraction procedure was repeated two times and the combined upper phases were concentrated by rotary evaporation, reconstituted in water, and dialyzed exhaustively against deionized water using Spectropor 3 dialysis tubing (MW cutoff=3500).

Anion-Exchange Chromatography. After dialysis the upper-phase extract was evaporated to dryness as above and dissolved in 50 mL of C/M/water (30:60:8) by a combination of warming (37° C.) and sonication. Insoluble material was removed by centrifugation at 1000×g for 10 min and re-extracted by sonication in an additional 50 mL of the same solvent. Following centrifugation as above the combined supernatants were loaded onto a DEAE-Sephadex column (300 mL bed volume; acetate form) and washed with 2 L of C/M/water (30:60:8) to remove all neutral lipids. The column was equilibrated with 500 mL methanol and the monosialoganglioside fraction eluted with 2 L 0.05 M $NH_4OAc$ in methanol. Subsequent removal of di-, tri-, and polysialosylgangliosides was achieved by eluting batch wise with 0.15 M, 0.45 M, and 1.0 M $NH_4OAc$, respectively. The eluted ganglioside fractions were dried by rotary evaporation, dialyzed against water, and dried as above.

Purification of Monosialogangliosides from HL60 Cells:

High Performance Liquid Chromatography. The monosialoganglioside fraction was solubilized in 10 mL of IHW and transferred from the evaporation flask to a 15 mL tube. The sample was completely dried under $N_2$ using an N-EVAP (Organomation Inc.) and reconstituted in 2 mL of IHW by sonication. The sample was injected onto a preparative Iatrobead column (6RS-8010; 0.8×60 cm; Iatron Laboratories Inc., Kanda/Tokyo, Japan) pre-equilibrated with IHW (55:40:5), and subjected to a linear gradient from IHW 55:40:5 to 55:25:20 with a flow rate of 1 mL/min. 4 mL fractions were collected over 400 min. Each fraction was spotted onto an HPTLC plate, developed in an appropriate solvent system (described below), visualized by spraying with 0.5% orcinol in 2N sulfuric acid, and pooled according to migration. Pooled fractions containing more than one band by TLC were dried under $N_2$, resolubilized in 1 mL of IHW, and injected onto a semi-preparative Iatrobead column (0.4×60 cm). A linear gradient from IHW 55:40:5 to 55:25:20 over 200 min with a flow rate of 0.5 mL/min was used. 1 mL fractions were collected and pooled according to HPTLC migration. Fractions containing a single band by HPTLC were labeled according to order of migration in $C/M/0.5\% CaCl_2$ (50:55:19); i.e., the fastest migrating band was labeled #1 and the slowest #20. Fractions containing multiple bands were further purified by preparative HPTLC.

High Performance Thin Layer Chromatography.

Monosialoganglioside fractions that were not resolved into single bands by HPTLC were separated by preparative HPTLC. Fractions within bands 1 to 7 were resolved in a solvent system of $C/M/0.5\% CaCl_2$ (50:40:10). Fractions within bands 8–14 were resolved in $C/M/0.5\% CaCl_2$ (50:55:19). Fr. 12 and 13 were further resolved (into Fr. 12-1 through 12-5 and 13-1 through 13-3 respectively) using a solvent system of isopropanol/water/$NH_4OH$ (6:3.2:1). Preparative TLC was performed by streaking 50 $\mu$L of sample across a 10×20 cm HPTLC silica gel plate (silica gel 60; EM Science, Gibbstown, N.J.), dried, and developed in the appropriate solvent system. Plates were dried, and bands were visualized by spraying with 0.03% primulin in 80% acetone. Bands were marked with a pencil under UV light. Marked bands were scraped from the plate using a razor blade, and gangliosides were extracted from the silica by sonicating for 20 min in IHW (55:25:20;2 mL per band). The silica was removed by centrifuging at 1000×g for 10 min, re-extracted as above, and the combined supernatants were dried under $N_2$. Samples were cleaned up using 1 cc tC-18 Sep-Pak cartridges (Waters, Milford, Mass.) by first dissolving the sample in 1 mL of PBS and then applying it to a column preequilibrated with PBS after sequentially washing with 5 mL of methanol and 5 mL of water. Once the sample was retained, the column was washed with 10 mL of water followed by 10 mL 50% methanol, and eluted in 10 mL of 100% methanol. The sample was dried under $N_2$, dissolved in 1 mL of IHW (55:25:20), and injected onto an Iatrobead column (0.4×60 cm) as above using a linear gradient from IHW 55:40:5 to 55:25:20 for 100 min at a flow rate of 1 mL/minute. One mL fractions were collected and visualized by HPTLC using the orcinol-sulfuric acid reaction. Orcinol-positive fractions were pooled and dried under $N_2$ prior to structural analysis.

Antibody Preparation

Balb/c mice are immunized by human neutrophils or HL60 cells by either intravenous or intraperitoneal repeated injections followed by a booster injection with monosialogangliosides containing myelorollin fraction adsorbed on *Salmonella minnesota* as previously described (Fukushi et al., 1984, J. Biol. Chem. 259:10511–10517; Nudelman et al., 1988, J. Biol. Chem. 263:13942–13951). After three days of booster injections, spleen cells were harvested and fused with NS-1 and the hybridoma was screened through a binding assay with 98-wells coated with purified myelorollin and those coated with $SLe^x$ or sialosyl paragloboside. Hybridoma secreting antibodies that react specifically with a myelorollin coated plate, but not with $SLe^x$ or sialosyl paragloboside coated plates, were cloned. Expansion of a clone followed by recloning with the specific reactivity of myelorollin is necessary.

Therapeutic Administration

The anti-inflammatory myelorollin compositions of the present invention are administered to a subject in need thereof for prophylactically preventing inflammation or relieving it after it has begun. The subject myelorollin compositions are preferably administered with a pharmaceutically acceptable carrier, such as included in liposomes or bound to carrier specific molecules with the appropriate design, the nature of which differs with the mode of administration. For example, oral administration usually requires a solid carrier, although "mimetics" of myelorollin are constructed when orally administered, while intravenous administration usually requires a liquid salt solution carrier or liposome suspension. Typically, injectable compositions are prepared as liquid solutions or suspensions; solid forms suitable for solution in, or suspension in, liquid vehicles prior to injection may also be prepared. The compounds may also be emulsified or the active ingredient encapsulated in liposome vehicles, which is more desirable for display of higher activity.

Suitable vehicles are, for example, water, saline, dextrose, glycerol, ethanol or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, for example, Remington's Pharmaceutical Sciences, Mack Publishing Company, Easton, Pa., 17th edition, 1985.

Pharmaceutically acceptable formulations may employ a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject myelorollin molecules directly in transdermal formulations with permeation enhancers such as DMSO. Other topical formulations can be administered to treat dermal inflammation. In addition, transmucosal administration may be effected using penetrants such as bile salts or fusidic acid derivatives optionally in combination with additional detergent molecules. These formulations are useful in the preparation of suppositories, for example, or nasal sprays. For suppositories, the vehicle composition will include traditional binders and carriers, such as polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject ligands by the nasal mucosa.

Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose to be administered, it will be noted that it may not be desirable to completely block all selectin molecules. In order for a normal inflammatory process to proceed, at least some of the white blood cells or neutrophils must be brought into the tissue in the areas where any wound, infection or disease state is occurring. The amount of the selectin ligands administered as blocking agents must be adjusted carefully based on the particular needs of the patient while taking into consideration a variety of factors such as the type of disease that is being treated.

Where the anti-inflammatory composition of the claimed invention is an antibody directed against a myelorollin, a pharmaceutically acceptable diluent can be employed and the antibody should be "humanized" and Fab fragmented. The particular pharmaceutically acceptable diluent employed is not critical thereto. Examples of such diluents include physiological saline, Ringer's solution, vitamin cocktail, and amino acid vitamin cocktail.

The pharmaceutically effective amount of the antibodies of the present invention to be administered will vary depending upon the age, weight, and sex of the subject to be treated. Generally, the pharmaceutically effective amount is about 1.0 to 5.0 μg/100 g body weight per one injection. Generally, from 5 to 10 injections of the antibodies are employed but the present invention is not limited thereto.

The compounds of the present invention are useful to treat a wide range of diseases, for example autoimmune diseases such as rheumatoid arthritis and multiple sclerosis. The compositions of the invention are applicable to treat any disease state wherein the immune system turns against the body causing the white cells to accumulate in the tissues to the extent that they cause tissue damage, swelling, inflammation and/or pain, particularly chronic inflammatory conditions that are E-selectin mediated.

Formulations of the present invention might also be administered to prevent the undesirable after effects of tissue damage resulting from acute inflammatory conditions inducing heart attacks. This is particularly desirable in combination with P-selectin inhibitors or P-selectin ligands, since P-selectin, but not E-selectin, plays a major role in acute inflammatory responses such as heart attacks or strokes. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors, a type of selectin, within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from acute physical trauma may be treated with formulations of the invention in order to relieve the amount of inflammation and swelling which normally result after an area of the body is subjected to severe trauma. Other conditions treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Various compositions comprising of: (1) a myelorollin: (A) Fr. 10-2, (B) a mixture of Fr. 10-1 and Fr. 10-2, or (C) Fr. 14, and (2) a pharmaceutically acceptable carrier such as, but not limited to: (D) polyalkylene glycol, (E) triglyceride, (F) fatty oil, (G) synthetic fatty acid ester, (H) liposome, (I) carboxymethyl cellulose, (J) sorbitol, or (K) dextran are administered in a therapeutically effective dosages thereof to patients suffering from an inflammatory disease such as, but not limited to, arthritis, rheumatoid arthritis, multiple sclerosis. These administrations are useful in curing ameliorating such diseases.

6. EXAMPLE

We previously detected in neutrophils and human promyelogenous leukemia HL60 cells the presence of polylactosamine gangliosides with terminal $\alpha 2 \rightarrow 3$ sialylation and $\alpha 1 \rightarrow 3$ fucosylation at various internal (but not the penultimate) GlcNAc residues. We refer to these compounds having the saccharide sequence of such gangliosides collectively as "myelorollin". By contrast, $SLe^x$-$Le^x$, determinants without internal $\alpha 1 \rightarrow 3$ fucosylation of polylactosamine chain were absent in these cells. In this study, we examined the activities of a series of myelorollin (A, B, C, D, X, Y, supra) to bind to cause adhesion and rolling of E-selectin expressing cells. The adhesion studies were carried under both static and dynamic flow conditions. Whereas rolling of E-selectin expressing cells on ganglioside coated surfaces were carried out under dynamic flow conditions.

The following may be concluded from this study. $SLe^x$-containing structures do not cause rolling, are virtually absent in neutrophils and HL60 cells, and have no physiological role in rolling, adhesion and extravasation of neutrophils. It is not $SLe^x$-containing structure, but rather a group of non-$SLe^x$-containing structures collectively called "myelorollin" (i.e., unbranched polylactosamine with terminal α2→3 sialylation and internal fucosylation [at various GlcNAc residues except for the penultimate GlcNAc alone]) which are responsible for causing rolling, adhesion and extravasation of neutrophils. Various types of myelorollin in a mixture synergistically cause E-selectin-dependent rolling and adhesion as compared with a singular molecule of myelorollin. Myelorollin is the major glycan and ganglioside of HL60 cells and human leukocytes. Blocking of myelorollin function can be achieved by a minimal essential structure involving in myelorollin that causes rolling and adhesion dependent on E-selectin. Antibodies highly specific to saccharide sequence of myelorollin can be readily prepared, selected, and used for anti-inflammatory drug preparation.

6.1 Materials and Methods

GSLs and monosialogangliosides

Table 1 shows the structures of the gangliosides (identified as Fr. or Str.) disclosed herein. Structures of the gangliosides were verified by $^1$H-NMR, $^+$ion FABMS, and ES-MS with CID of permethylated compounds as described previously (Stroud et al., 1995, Biochem. Biophys. Res. Comm. 209:777–787; Stroud et al., 1996, Biochemistry 35:758–769; Stroud et al., 1996, Biochemistry 35:770–778). Structures of Fr. 9-1, 9-2, 10-1, and 10-2 were further confirmed by endo-β-galactosidase digestion (Fukuda et al., 1979, J. Biol. Chem. 254:5458–5465), methylation analysis, and $^+$ion FABMS.

TABLE 1

Gangliosides used for E-selection binding study.

| Fr.* | Str. | Structure | Cer ion |
|---|---|---|---|
| 7 | 1 | NeuAcα3Galβ4GlcNAcβ3Galβ4GlcNAcβ3Galβ4GlcβCer | 536 |
| 8 | 2 | Galβ4GlcNAcβ$_6$<br>　　　　　Galβ4GlcNacβ3Galβ4GlcNAcβ3Galβ4GlcβCer<br>　　　　　　3<br>　　　　　NeuAcα | 658/660 |
| ** | 3 | Galβ4GlcNAcβ3Galβ4GlcNAcβ3Galβ4GlcβCer<br>　　　　3　　　　　　　　3　　　　　　　　3<br>　　　NeuAcα　　　　　Fucα　　　　　Fucα | |
| 10-1 | 4 | Galβ4GlnNAcβ3Galβ4GlcNAcβ3Galβ4GlcNAcβ3Galβ4GlcβCer<br>　　　　　　　　3　　　　　　　　　　3<br>　　　　　　　NeuAcα　　　　　　　　Fucα | 546/548 |
| 10-2 | 5 | Galβ4GlcNAcβ3Galβ4GlcNAcβ3Galβ4GlcNAcβ3Galβ4GlcβCer<br>　　　　　　　　3　　　　　　　　　　　　　　　3<br>　　　　　　NeuAcα　　　　　　　　　　　　Fucα | 546/548 |
| 12-2 | 6 | Galβ4GlcNAcβ3Glaβ4GlcNAcβ3Galβ4GlcNAcβ3Galβ4GlcNAcβ3Galβ4GlcβCer<br>　　　　　　　3　　　　　　　　　　　3<br>　　　　NeuAcα　　　　　　　Fucα　　　　(same as ACFH-18 antigen) | 548 |
| 13-1‡ | 7 | Galβ4GlcNAcβ3Galβ4GlcNAcβ3Galβ4GlcNAcβ3Galβ4GlcNAcβ3Galβ4GlcβCer<br>　　　　　　3　　　　　　　　3　　　　　　　　3<br>　　　NeuAcα　　　　　Fucα　　　　　Fucα | 548 |
| 13-1 | 8 | Galβ4GlcNAcβ3Galβ4GlcNAcβ3Galβ4GlcNAcβ3Galβ4GlcNAcβ3Galβ4GlcβCer<br>　　　　　　3　　　3　　　　　　　　3<br>　　　NeuAcα　Fucα　　　　　Fucα | 548 |
| 14§ | 9 | Galβ4GlcNAcβ3Galβ4GlcNAcβ3Galβ4GlcNAcβ3Galβ4GlcNAcβ3Galβ4GlcNAcβ3Galβ4GlcβCer<br>　　　　　　3　　　　　　　　　　3<br>　　　NeuAcα　　　　　　　　　Fucα | 548 |
| 14 | 10 | Galβ4GlcNAcβ3Galβ4GlcNAcβ3Galβ4GlcNAcβ3Galβ4GlcNAcβ3Galβ4GlcNAcβ3Galβ4GlcβCer<br>　　　　　　3　　　　　　　　　　　　　　　3<br>　　　NeuAcα　　　　　　　　　　　　Fucα | 548 |
| 14 | 11 | Galβ4GlcNAcβ3Galβ4GlcNAcβ3Galβ4GlcNAcβ3Galβ4GlcNAcβ3Galβ4GlcNAcβ3Galβ4GlcβCer<br>　　　　　　3　　　　　　　　3　　　　　　　　3<br>　　　NeuAcα　　　　　Fucα　　　　　Fucα | 660 |
| 14 | 12 | Galβ4GlcNAcβ3Galβ4GlcNAcβ3Galβ4GlcNAcβ3Galβ4GlcNAcβ3Galβ4GlcNAcβ3Galβ4GlcβCer<br>　　　　　　3　　　　　　　　　　3　　　　　　　　　　3<br>　　　NeuAcα　　　　　　　Fucα　　　　　　　Fucα | 660 |

*Fraction numbers correspond to those used in our previous paper (Stroud MR, et al., submitted MS).
**This structure was isolated from colonic adenocarcinoma (Fukushi et al., 1984, J. Biol. Chem. 259:10511–10517).
†Molar ratio of Str. 4 and 5 present in Fr. 10 was 1:1.
‡Molar ratio of Str. 7 and 8 present in Fr. 13-1 was 10:1.
§Molar ratio of Str. 9, 10, 11, and 12 present in Fr. 14 was 5:1:3:1.

Cells and Binding Assay

CHO cells transfected with E-selectin cDNA were established as described previously (Handa, et al., 1995, Int. J. Oncol. 6:773–781). E-selectin expressing transfectants were isolated by cytofluorometry using anti-E-selectin mAb E1A. Inhibition of E-selectin-dependent cell adhesion was performed using anti-E-selectin mAb E1C at 10 μg/mL concentration. These mAbs were established through immunization of BALB/c mice with NS1 cells expressing E- or P-selectin.

E-Selection-Dependent Cell Adhesion to Various GSLs Under Static Conditions on Plastic Plate Static adhesion assay using 96-well plates: Poly-LacNAc gangliosides (e.g. SLe$^x$-Le$^x$ and Fr. 9, 10-1, 10-2 and 12-2), dissolved in 50% ethanol, were serially diluted in 96-well plates (the first well contained 200 ng), and plates were dried at 37° C. for 5 hr. Plates with similar serial dilutions of poly-LacNAc gangliosides were prepared for control cell adhesion in the presence of mAb E1C. E-selectin expressing CHO cells (Handa et al., 1995, Int. J. Oncol. 6:773–781) were metabolically labeled with [$^3$H]thymidine and incubated for 2 days. Cell suspension ($2 \times 10^6$ per mL) was prepared by 2 mM EDTA treatment of cultured cells. A 50 μL aliquot of this cell suspension (containing $1 \times 10^5$ cells; approximately 5000 cpm) was added to each well and incubated for 1 hr. As a control, EDTA-harvested cells were washed with DMEM and incubated with mAb E1C on ice for 30 min, followed by preparation of cell suspension as above, but containing 10 μg mAb E1C per mL. Aliquots were added to each well and incubated as above. Cells were washed three times with PBS by inversion of the plate on blotting paper. Adherent cell count as measured by $^3$H activity was determined.

E-Selectin-Dependent Cell Adhesion to Gangliosides Affixed on Polystyrene Beads Under Static Conditions In order to observe static adhesion with the same matrix used for dynamic adhesion assay, the following procedure was used. Polystyrene latex beads of 1 μm or 4 μm diameter (IDC Spheres™; IDC, Portland, Oreg.), affixed to objective microscope slides, were used as carriers of poly-LacNAc GSLs. 30 μL of the 4 μm diameter bead suspension (containing $2 \times 10^9$ beads/mL) or 60 μL of 1 μm bead suspension (containing $1 \times 10^{11}$ beads/mL) were placed in Eppendorf tubes and washed three times with absolute ethanol. Sedimented 4 μm beads were suspended in 500 mL ethanol, and sedimented 1 μm beads were suspended in 2 mL ethanol. 1 μL aliquots of these suspensions were placed on freshly opened microscope slides (Labcraft Superfrost® Plus, Curtin Matheson Scientific, Houston, Tex.). Beads were distributed homogeneously on the glass surface within a circular spot having a diameter of approximately 1 cm. Slides were heated at 150° C. for 50 sec, which caused the beads to adhere strongly to the surface such that they could not be washed off by water stream at various velocities. Gangliosides dissolved in isopropanol-hexane-water at the same molar concentration were applied to beads affixed to the slides; namely, 1 μL aliquots containing 50–100 ng ganglioside were placed on the center of the circular spot. The ganglioside thus became affixed to the bead surface. Slides were immersed in 3% BSA in PBS for 1 hr at room temp, and washed three times with PBS containing $Ca^{2+}/Mg^{2+}$.

Slides were overlaid with $5 \times 10^5$ CHO cells freshly harvested and suspended in RPMI culture medium for 15 min without moving. Washing three times with RPMI was usually sufficient to eliminate non-adherent cells from beads. However, careful microscopic examination had to be repeated until the cells placed on control beads were washed out. Slides were then fixed with 1% glutaraldehyde in PBS and number of cells adhered to the layer of poly-LacNAc ganglioside-coated beads were counted.

E-Selectin-Dependent Cell Rolling and Adhesion Through Various GSLs Under Dynamic Flow Conditions Polystyrene beads ($4.2 \pm 3.7\%$ μm or 1 μm) were prepared and affixed to microscope slides using procedures described above. Gangliosides dissolved in IHW at the same molar concentration were applied to beads affixed on the slides; namely, 1 μL aliquots containing 50–100 or 0.05–0.1 ng ganglioside were placed on the center of a circular spot.

Slides were immersed in PBS with 3% BSA for 1 hr at room temperature and washed three times with PBS containing $CA^{2+}/Mg^{2+}$. Slides were placed in a parallel plate laminar flow chamber connected to an infusion pump (model 935, Harvard Apparatus, Cambridge, Mass.). The assembly, as described by Lawrence et al., 1990, Blood 75:227–237; Lawrence and Springer, 1991, Cell 65:859–873, simulates the flow shear stress present in physiological microvascular environments. A laminar flow with defined rate and wall shear stress is achieved by manipulation of the infusion pump, which is connected to the inlet of the flow chamber. A suspension of E- or P-selectin-expressing CHO cells ($1 \times 10^5$ cells/mL in FIGS. 2A–2E, $2 \times 10^5$ cells/mL in FIG. 5A, $5 \times 10^5$ cells/mL in FIGS. 5B, 4A and 4B), freshly harvested from culture with EDTA, washed, and resuspended in RPMI medium containing 1% FCS, was infused into the assembly at various laminar flow rates. Cell movements were observed under inverted phase-contrast microscope (Diaphot-TMD, Nikon) and recorded by time-lapse videocassette recorder. Cell rolling and adhesion were observed, and numbers of rolling and adherent cells during a 2 min. period at shear stresses, from 0.6 to 12.0 dynes/cm$^2$ were counted from at least 10 fields on videotape. Wall shear stress (T) was calculated by the equation described by Lawrence et al., 1990, Blood 75:227–237 and Lawrence et al., 1987, Blood 70: 1284–1290: T=3 μQ/2 ba$^2$, where μ=coefficient of viscosity (1.0 cP), Q=volumetric flow rate (cm$^3$/sec), a=half channel height (in this case, $5.7 \times 10^{-3}$ cm), and b=channel width (1.3 cm).

Demonstration of Direct Binding of E- or P-Selectin to Myelorollin Gangliosides by Fluorometric Analysis $5 \times 10^6$ polystyrene beads (diameter $4.2 \pm 3.7\%$ μm) (IDC Spheres™; IDC, Portland, Oreg.) were washed with ethanol by centrifugation. 1 μg of GSL in 50 μL of ethanol was added to the washed beads and the mixture was evaporated under nitrogen stream. The beads were resuspended in PBS(+) with 1% BSA and washed twice by centrifugation. Washed beads were blocked with PBS(+) with 3% BSA at room temperature for 2 hr. After centrifugation, beads were resuspended in PBS(+) with 1% BSA and 0.1% azide and stored at 4° C. Yellow-green fluorescent sulfated latex beads (diameter 1 μm) (Molecular Probes, Inc., Portland, Oreg.) were coated with goat anti-human IgG (Fc-fragment specific) antibody (Jackson Immunoresearch Lab, West Grove, Pa.) according to manufacturer's protocol. After washing three times with PBS, beads were blocked with PBS with 3% BSA at 4° C. for 2 hr. Blocked beads (about $5 \times 10^8$) were mixed with 1.5 mL of E- or P-selectin-Ig fusion protein containing culture supernatant (about 1 μg/mL fusion protein) from CHO transfectants (Handa et al., 1995, Int. J. Oncol. 6:773–781) with a blood mixer at 4° C. for 6–18 hr. This mixing procedure was repeated 3 times more using new culture supernatant containing the fusion protein.

After washing with PBS, beads were incubated in 1 mL PBS containing 50 μg human IgG (Jackson Immunoresearch). For preparation of control beads, human IgG was used at 1 μg/mL, instead of fusion protein. The ganglioside-coated beads were mixed with the fluorescent beads at room temperature for various durations. The resulting suspension was subjected to flow cytometric analysis. Conditions of each assay are detailed below.

6.2. Results

E-Selectin-Dependent Adhesion Under Static Conditions

Adhesion of E-selectin expressing cells to myelorollin gangliosides and SLe$^x$-containing gangliosides under static conditions was studied by two different methods as described in Materials & Methods. In one method, gangliosides were coated directly on wells of 96-well plates followed by blocking by BSA, and [$^3$H]thymidine-labeled E-selectin expressing cells were added and incubated in the presence and absence of anti-E-selectin antibodies. Results showed that E-selectin expressing cells bind to surfaces coated with SLe$^x$-Le$^x$, but not to these coated myelorollin (Fr. 10-1, 10-2, 9 and 12-2), under static conditions (FIG. 1A). The presence of mAb E1C in the binding reaction abolished binding of E-selectin expressing cells to surfaces coated with SLe$^x$-Le$^{x\,l}$.

Additional details of the experiment whose data are shown in FIG. 1A are as follows: SLe$^x$-Le$^x$ and poly-LacNAc gangliosides (Fr. 9, 10-1, 10-2, and 12-2) dissolved in 50% ethanol were appropriately diluted and coated on wells of 96-well plates (amounts of 25 to 200 ng as shown on abscissa). Wells were dried at 37° C. for 5 hr. Two identical plates (1 and 2) were prepared as follows. In plate 1, 50 μL aliquots of RPMI containing 1×10$^5$ E-selectin expressing CHO cells metabolically labeled with [$^3$H] thymidine were added to the wells. In plate 2, 50 μl aliquots of RPMI containing 1×10$^5$ E-selectin expressing CHO cells and mAb E1C cells preincubated with anti-E-selectin mAb E1C (10 μg Ig per mL) were added to the wells. Plates 1 and 2 were incubated for 25 min. and washed with PBS as follows. Each well was filled with 200 μL of PBS, carefully shaken, and plates were inverted on blotting paper for 10 min. All non-adherent cells were sedimented and absorbed on the blotting paper. Adherent cells remaining on wells were counted. Cell numbers were calculated based on measured radioactivity.

The other method used polystyrene beads (1 μm diameter) affixed on glass microscope slides. Gangliosides were quantitatively adsorbed on the beads. To this matrix, non-radiolabeled E-selectin expressing CHO cells were added, incubated, washed and the number of adhered cells counted as described in Materials and Methods. The results were as follows. SLe$^x$-Le$^x$ (VI$^3$NeuAcV$^3$FucIII$^3$FucnLc$_6$Cer) showed slightly higher adhesion of cells than Fr. 13-1 (X$^3$NeuAcVII$^3$FucV$^3$FucnLc$_{10}$Cer; Str. 7). Fr. 14 (a mixture of Str. 9, 10, 11, and 12) showed moderate adhesion (slightly lower than SLe$^x$-Le$^x$). Under the same conditions, Fr. 10-1 (VIII$^3$NeuAcV$^3$FucnLc$_8$Cer; Str. 4), Fr. 10-2 (VIII$^3$NeuAcIII$^3$FucnLc$_8$Cer; Str. 5), and Fr. 12-2 (X$^3$NeuAcVII$^3$ FucnLc$_{10}$Cer) showed much weaker adhesion of cells than Fr. 13-1 or Fr. 14 (FIG. 1B). Sialosyls poly-LacNAc without internal fucosylation (e.g. VI$^3$NeuAcnLc$_6$Cer; Fr. 7) showed no adhesion of cells.

Important findings shown in FIGS. 1A and 1B are that, under static conditions: 1) SLe$^x$-Le$^x$ show much stronger adhesion activity than myelorollin (Fr. 13-1 and 14); 2) sialosyl-poly-LacNAc with single internal α1→3 fucosylation (Fr. 9, 10-1, 10-2 and 12-2) and sialosyl-poly-LacNAc without fucosylation (Fr. 7) show little or no adhesion activity; and 3) mAb E1C blocks adhesion of E-selectin expressing cells to surfaces coated with SLe$^x$-Le$^x$.

E-Selectin-Dependent Cell Binding to Gangliosides Affixed to Polystyrene Beads Under Dynamic Flow Conditions In contrast to the results described above, rolling and adhesion of E-selectin expressing CHO cells occurred on beads coated with Fr. 10, 13-1, and 14 (containing Str. 4–5, Str. 7–8, and Str. 9–12, respectively) under dynamic flow conditions. Polystyrene beads were affixed to glass microscope slides. Various gangliosides were coated as described in Materials & Methods. Slides were blocked by placing 1% or 2% bovine serum albumin in PBS for 1 hr, and then assembled in a parallel laminar-flow chamber as described in Material & Methods. E-selectin expressing CHO cells were freshly harvested and suspended (1×10$^5$ cells) in RPMI medium. The cell suspensions were placed in an infusion pump connected to the flow chamber, and infused into the assembly at various laminar flow rates. Cell movements were observed under phase-contrast microscope and recorded by videocassette recorder. Numbers of rolling cells in at least 10 microscope fields were counted, and average numbers were recorded. The results are shown in FIG. 4C.

Cell rolling was strongest on beads coated with Fr. 10 or 14, which have myelorollin structure and lack SLe$^x$ epitope (FIG. 4C). Rolling was particularly evident at 2.4 and 4.8 dynes/cm$^2$ shear stresses. No rolling was observed on SLe$^x$-Le$^x$ coated beads regardless of shear stress. This is in striking contrast to significant rolling followed by adhesion observed on beads coated with myelorollin Fr. 13-1 or Fr. 14. Under dynamic flow conditions beads coated with SLe$^x$-Le$^x$ did bind cells, but to lesser extent than beads coated with the myelorollin fractions. There was no cell adhesion to beads coated with Str. 1 or 2.

Figure 6A:
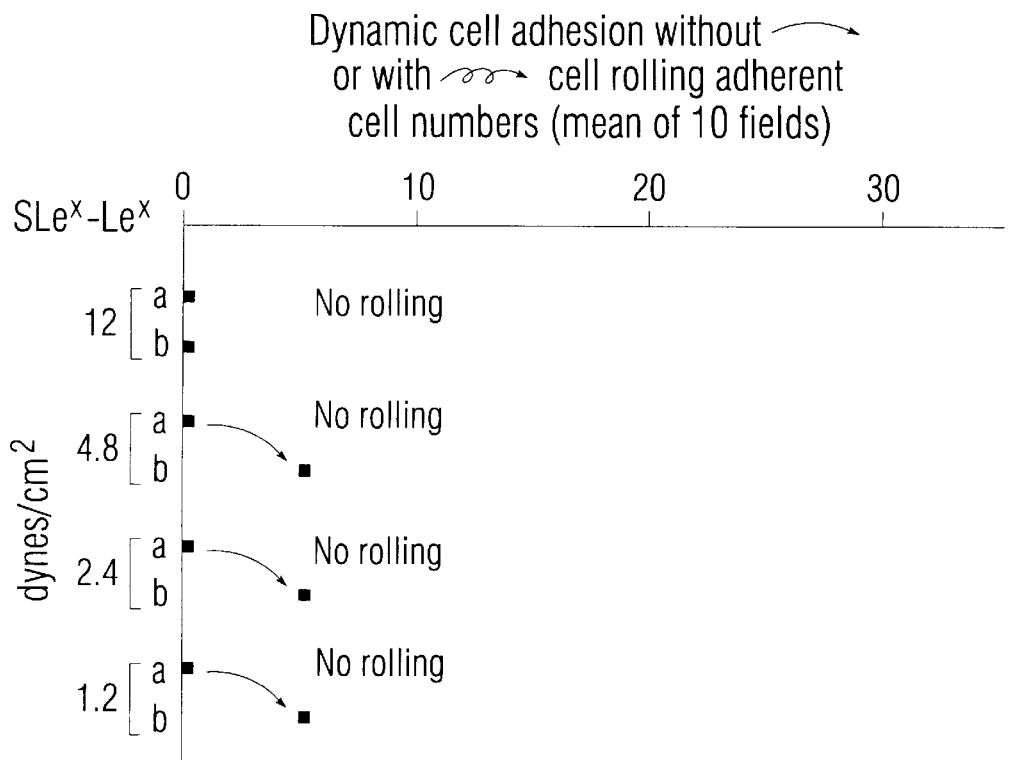
Figure 6B:
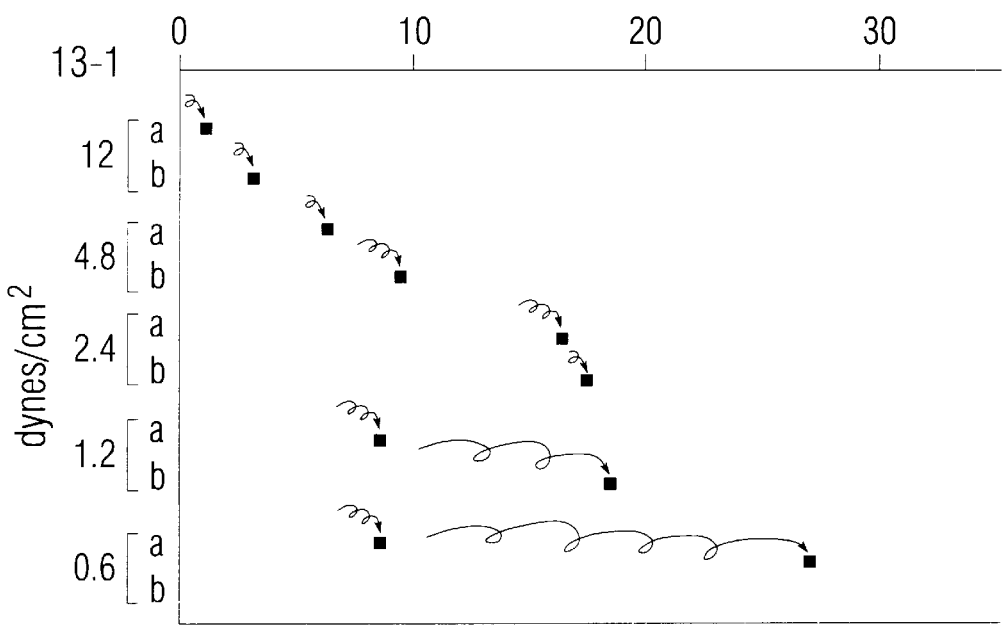
Figure 6C:
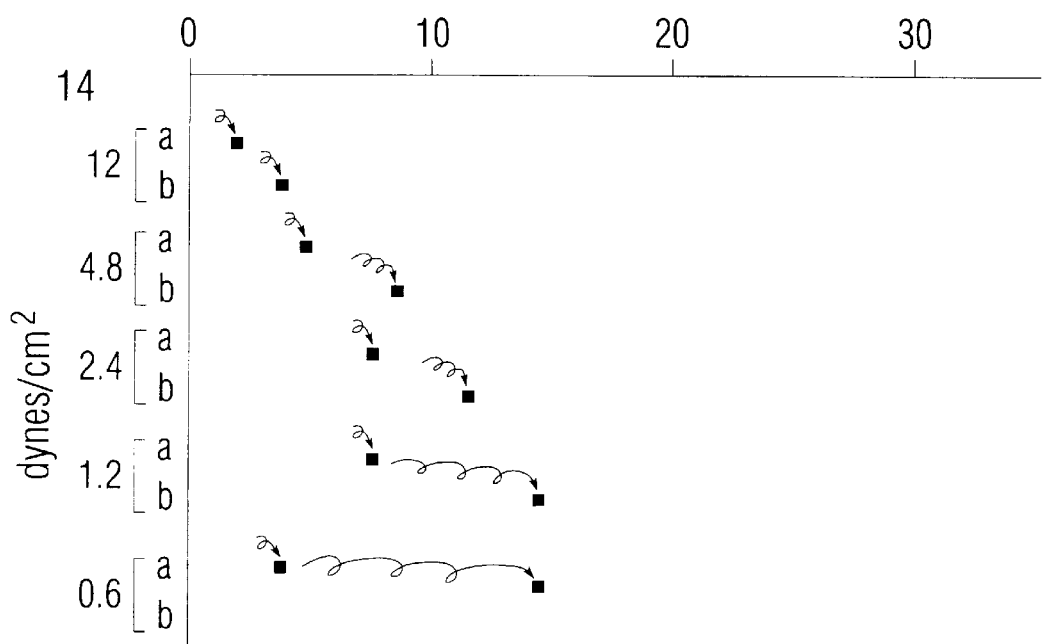
Figure 6D:
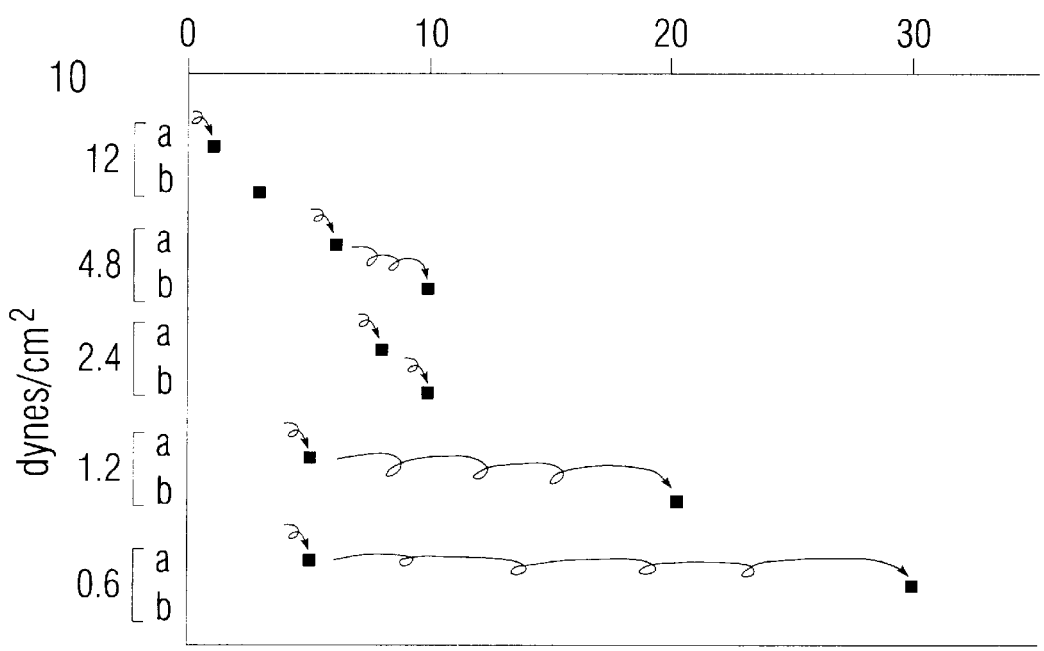

E-selectin dependent plain rolling, rolling followed by adhesion, and adhesion in a dynamic flow system under various shear stresses are compared in FIGS. 6A and 6B. Little or no rolling was observed on SLe$^x$-Le$^x$ coated beads regardless of shear stress (12 to 1.2 dynes/cm$^2$). A small number of cells (less than 5/field) adhered but showed no rolling. By contrast, significant numbers of plain rolling cells occurred on the myelorollin coated beads under shear stress conditions (4.8 and 12 dynes/cm$^2$). The number of cells showing plain rolling and rolling followed by adhesion was highest at 2.4 dynes/cm$^2$ for all myelorollin tested (Fr. 13-1, Fr. 14, and Fr. 10). At shear stress conditions (0.6 and 1.2 dynes/cm$^2$) the number of rolling cells followed by adhesion greatly increased.

Referring to FIGS. 6A and 6B in more detail, the number of plain rolling cells and rolling cells followed by adhesion under defined wall shear stress conditions (12, 4.8, 2.4, 1.2 and 0.6 dynes/cm$^2$) is indicated by the block with the coiled arrow symbol. FIG. 6A: Panel I, cell adhesion to SLe$^x$-Le$^x$ (Sdiy$^2$). There was no rolling under any of the shear stress conditions tested. Low level of adhesion without rolling was observed at 4.8 to 1.2 dynes/cm$^2$ shear stress. No variation in the number of adherent cells at different wall shear stresses. a, number of rolling cells; b, non-rolling adherent cell. Panel II, plain rolling cell and rolling cell followed by adhesion to beads coated with ganglioside Fr. 13-1 (Str. 7). Rolling was maximal at 2.4 dynes/cm$^2$, and declined at lower shear stress. a, number of rolling cells; b, number of rolling cells followed by adhesion. FIG. 6B: Panel III, plain rolling cell and rolling cell followed by adhesion to beads coated with Fr. 14, which is a mixture of Structures 9, 10, 11 and 12. High rolling followed by adhesion were observed at 2.4 to 1.2 dynes/cm$^2$. a, number of rolling cells; b, number of rolling cells followed by adhesion. Panel IV, plain rolling cell and rolling cell followed by adhesion to beads coated with a mixture of Fr. 10-1 and 10-2, which is a mixture of Structures 4 and 5. Maximal rolling followed by adhesion were observed at 2.4 dynes/cm$^2$. a, number of rolling cells; b, number of rolling cells followed by adhesion.

Rolling and Adhesion of E-Selectin Expressing Cells Under Dynamic Flow Conditions FIGS. 2A to 2E show the results of rolling and adhesion of E-selectin expressing CHO cells under shear stress conditions similar to those obtained in the experiment described above. FIG. 2A shows that there were adherent, but not rolling cells on SLe$^x$-Le$^x$ coated beads at all shear stresses.

FIG. 2B shows the results of rolling and adhesion of cells on Fr. 12-2 coated beads. Rolling was highest at 4.8 dynes/cm$^2$. Both rolling and adhesion were lower than those on beads coated with Fr. 13-1 or 14 (FIGS. 2C and 2E, respectively), but comparable to that on beads coated with SLe$^x$-Le$^x$.

FIG. 2C shows the results of rolling and adhesion of cells on Fr. 13-1 (Str. 7) coated beads. The number of rolling cells was greater at 4.8 and 2.4 than at 1.2 dynes/cm$^2$.

FIG. 2D shows the results of rolling and adhesion of cells on Fr. 13-1 coated beads. The number of rolling cells was highest at 4.8 dynes/cm$^2$. Adhesion was higher and rolling FIG. 2E shows the results of rolling and adhesion of cells on Fr. 14 coated beads. Rolling and adhesion were highest at 2.4 and 4.8 dynes/cm$^2$. Rolling was lower at 1.2.

Myelorollin Analogs Showed Higher E-Selectin-Dependent Rolling and Adhesion Than SLe$^x$-Le$^x$ Under Dynamic Flow Conditions at Physiological Shear Stress 100 ng of poly-LacNAc ganglioside (Fr. 13-1, Fr. 14 or SLe$^x$-Le$^x$) was adhered to beads affixed to microscope slides, which were then placed in the dynamic flow system as described in Material & Methods. The rolling and adhesion of E-selectin expressing CHO cells was determined in this system under various shear stresses. Trends of cell adhesion to poly-LacNAc gangliosides coated beads were essentially similar for the 4 μm and 1 μm beads (FIGS. 2C and 2D, respectively). Fr. 13-1 or Fr. 14 produced strong rolling and adhesion at 4.8 or 2.4 dynes/cm$^2$. Number of rolling cells was lower at 1.2 dynes/cm$^2$ (FIGS. 2C, 2D and 2E). Number of adhering cells on beads coated with SLe$^x$-Le$^x$ was significantly lower than on those coated with Fr. 13-1 or 14. No rolling cells were observed with beads coated with SLe$^x$-Le$^x$ (FIG. 2A).

A series of experiments on rolling/adhesion of E-selectin expressing cells to various gangliosides under dynamic conditions indicate that SLe$^x$-containing structures do not cause rolling. Sialosyl poly-LacNAc having one α1→3 linked Fuc at different GlcNAc as found in Fr. 10 and 14 produced strong rolling. Fr. 13-1, which is essentially pure component having two α1→3 Fuc residues, also caused strong rolling. Rolling cells were counted, excluding adherent cells, and the results shown in FIG. 4C.

Mixtures of Myelorollin Causes Better Rolling and Adhesion Than Purified Myelorollin The data shown in FIGS. 3A, 4B, 4C, 5A, 5B, 6A and 6B of cell rolling and adhesion under dynamic conditions relate to mixtures of myelorollins (except the data relating to SLe$^x$-Le$^x$). Further studies indicate "myelorollin mixtures" display a much higher capability of causing E-selectin-dependent rolling followed by adhesion than purified myelorollin (see Table 2).

Myelorollin mixtures also have stronger adhesion activity than purified myelorollin under static conditions. For example, Fr. 11, a pure compound of Str. 6, shows weak adhesion of E-selectin expressing cells; whereas Fr. 10, a mixture of Str. 4 and 5, shows a remarkably strong adhesion of E-selectin expressing cells (FIG. 3A).

Direct Binding of Myelorollin to E- and P-Selectin Determined by Flow Cytometry

In our previous studies, poly-LacNAc gangliosides having two α1→3 Fuc residues (e.g., Fr. 12-3, 13-1, and 14) were only capable of binding E-selectin expressing cells under static conditions. We did not observe cell adhesion to poly-LacNAc gangliosides having a single α1→3 Fuc residue at internal GlcNAc (Fr. 9, 10, and 12-1) under static conditions (Stroud et al., 1995, Biochem Biophys Res. Commun 209:777–778; Stroud et al., Biochemistry 35:758–769; and Stroud et al., 1996, Biochemistry 35:770–778). These findings were confirmed by the data of subsequent experiments, which are shown in FIGS. 1A and 1B.

By contrast, under dynamic flow conditions, poly-LacNAc gangliosides having a single α1→3 Fuc residue at internal GlcNAc (Fr. 9, 10, and 12-1) bound to and caused strong rolling of E-selectin expressing cells. Since these myelorollin fractions are major cell surface components of neutrophils and HL60 cells, it is important to confirm their E-selectin binding ability by other methods.

Adhesion of E- or P-selectin-binding to various gangliosides was assessed by a novel, sensitive method using E- or P-selectin-coated fluorescent beads. Adhesion was determined by aggregation of polystyrene beads coated with myelorollin, and selectin-coated fluorescent beads. Gangliosides were coated on non-fluorescent polystyrene beads and mixed with fluorescent beads coated with E- or P-selectin in the presence or absence of EDTA. Since aggregation occurs under brief, strong agitation, the process is neither "static" nor "dynamic" adhesion, in which myelorollin is presented as immovable solid phase. Binding was determined by cytofluorometry. Binding index was defined as mean fluorescence intensity (MFI) of ganglioside fraction divided by MFI of sialylparagloboside (IV$^3$NeuAcnLc$_4$Cer).

The results are shown in FIG. 3A. The binding of myelorollin coated beads to E-selectin coated beads was completely abolished in the presence of EDTA; myelorollin coated beads were unable to bind to P-selectin coated beads. Beads coated with a mixture of Str. 4 and 5, which have no SLe$^x$ terminus but are internally α1→3 fucosylated at GlcNAc-III and GlcNAc-V, bound strongly to E-selectin coated beads. Beads coated with Fr. 13-1 (containing Str. 7 and 8 at a ratio of 10:1) and Fr. 14 containing myelorollin Str. 9–12 also showed clear binding to E-selectin coated beads. By contrast, beads coated with Fr. 7 (containing Str. 1) or Fr. 8 (containing Str. 2), which have no internal fucosylation, showed no binding to E-selectin coated beads. Beads coated with Str. 3, which has SLe$^x$ terminus with internal α1→3 fucosylation, did show binding to E-selectin coated beads as expected.

FIG. 3B shows inhibitory effect of an anti-E-selectin antibody on binding of E-selectin coated beads to beads coated with various myelorollin fractions. E1C was one of the anti-E-selectin mAbs selected based on inhibitory effect on E-selectin binding to HL60 cells. The inclusion of mAB E1C in the binding reaction essentially abolished binding of E-selectin coated beads to beads coated with any of the gangliosides tested (FIG. 3B).

Enhanced Adhesion and Rolling of Cells on Two poly-LacNAc Gangliosides Having fucosyl α1→3 Linked at Different GlcNAc Residues FIGS. 5A and 5B show the synergistic effects of combining myelorollins on adhesion and rolling of E-selectin expressing cells. Fr. 10-1 and 10-2 are poly-LacNAc gangliosides having α1→3 fucosylation at GlcNAc-V and GlcNAc-III respectively. Beads coated with 100 ng of either fraction caused comparable cell rolling and adhesion at 4.8 and 2.4 dynes/cm$^2$ (FIG. 5A, Plots 1 and 2). Beads coated with mixture of 50 ng each of Fr. 10-1 and 10-2 caused higher cell rolling and adhesion at these same shear stresses (Plot 3). Statistical significance of the differences between the three plots (P values from unpaired Student's t-test) are shown in the inset table on FIG. 5A.

The synergistic effect of a mixture of Fr. 10-1 and Fr. 10-2, as compared to either fraction alone, on cell rolling and adhesion was more evident when Fr. 10-1 and Fr. 10-2 were used at 1000-fold lower concentrations. (FIG. 5B). Fr. 10-2 at this low level (0.1 ng per spot) still produced some cell rolling and adhesion (FIG. 5B, Plot 2), but Fr. 10-1 did not (Plot 1). By contrast, a mixture of 0.05 ng each of Fr. 10-1 and 10-2 caused significant cell rolling and adhesion at physiological shear stress (2.4–4.8 dynes/cm$^2$) (Plot 3). Statistical significance between plots (P values from unpaired Student's t-test) are shown in the inset table on FIG. 5B.

Comparison of Cell Rolling and Adhesion on Low Contractions of SLe$^x$-Le$^x$ and a Mixture of Fr. 10-1 and Fr. 10-2

FIG. 4A shows that 0.05 ng of SLe$^x$-Le$^x$ (the compound which produced strongest adhesion under static conditions) caused no rolling or adhesion under dynamic conditions in two replicate experiments (Plots 1 and 2). By contrast, FIG. 4B shows that 0.05 ng each of Fr. 10-1 and Fr. 10-2 high cell rolling and adhesion at the same shear stresses (Plots 1 and 2). Further experiments showed 0.1 ng of SLe$^x$-Le$^x$ caused no 5cell rolling or adhesion.

6.3 Discussion

Expression of E- and P-selectin on ECs in response to inflammatory stimuli causes interaction of ECs with neutrophils or other leukocytes, resulting in rolling followed by adhesion and transendothelial migration of leukocytes. E-selectin-dependent rolling followed by adhesion and E-selectin-dependent adhesion have been thought to be mediated by recognition of SLe$^x$ epitope expressed on leukocytes by E-selectin. This concept was based on various observations which, however, did not include unequivocal chemical identification of the real carbohydrate epitope present on neutrophils. Human neutrophils, other leukocytes, and leukemic leukocyte cell lines (HL60 and U937) show strong reactivity with various mAbs previously claimed to be directed to SLe$^x$. However, quantities of SLe$^x$ chemically detectable in these cells are extremely small. $^+$Ion FABMS of permethylated side chains of N-linked structures in leukemic leukocytes gave a barely detectable m/z 999 signal, representing SLe$^x$ structure (Fukuda et al., 1984, J. Biol. Chem. 259:10925–10935). The presence of SLe$^x$ in side chains of N- or O-linked structures in neutrophils or myelogenous leukemia cells was assumed (Asada et al., 1991, Biochemistry 30:1561–1571; Patel et al., 1994, Biochemistry 33:14815–14824), but was not supported by unambiguous chemical analysis.

Our recent systematic studies on gangliosides of normal human leukocytes and promyelogenous leukemia HL60 cells has indicated that only unbranched monosialogangliosides having cores with >10 sugars are responsible for E-selectin binding (Stroud et al., 1995, Biochem. Biophys. Res. Commun. 209:777–787). Gangliosides with SLe$^x$ structure (e.g., IV$^3$NeuAcIII$^3$FucnLc$_4$Cer, VI$^3$NeuAcV$^3$FucnLc$_6$Cer, VI$^3$NeuAcV$^3$FucIII$^3$FucnLc$_6$Cer), which are abundantly present in various types of solid human cancer (Yang and Hakomori, 1971 J. Biol. Chem. 246:1192–1200; Fukushi et al., 1984, J. Biol. Chem. 259:10511–10517), were completely absent from leukocytes and HL60 cells. Among long-chain PLA lipids having 8-, 10-, or 12-sugar cores, structures having SLe$^x$ epitope without internal fucosylation (e.g. VIII$^3$NeuAcVII$^3$FucnLc$_8$Cer, X$^3$NeuAcIX$^3$FucnLc$_{10}$Cer, XII$^3$NeuAcXI$^3$FucnLc$_{12}$Cer) were completely absent. Instead, there were trace components having SLe$^x$ with internal fucosylation (e.g., X$^3$NeuAcIX$^3$FucVII$^3$FucnLc$_{10}$Cer) (Stroud et al., 1995, Biochem. Biophys. Res. Commun. 209:777–787). The major structures present in leukocytes and HL60 cells were a series of unbranched long-chain PLAs having terminal α2→3 sialylation and internal α1→3 fucosylation, with the representative structures A, B, C, D, X and Y shown below:

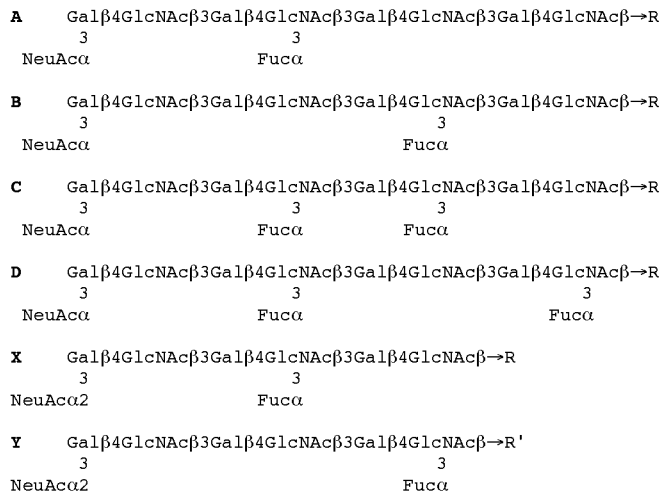

wherein → indicates covalent bond; R is a ceramide residue.

Structure A is common to Str. 4 and 6. Structure B is common to Str. 5 and 10. Structure C is common to Str. 7 and 11. Structure D is found in Str. 12. None of these four structures contains SLe$^x$ epitope.

Structure A was previously found in gangliosides isolated from chronic myelogenous leukemia cells (Fukuda et al., 1984, J. Biol. Chem. 259:10925–10935) and from human colonic cancer, and was identified as ACFH-18 antigen (Nudelman et al., 1988, J. Biol. Chem. 263:13942–13951). Structure A was also identified as being defined by mAb "VIM-2" (Macher et al., 1988, J. Biol. Chem. 263:10186–10191), and was once claimed to be the E-selectin binding epitope (Tiemeyer et al., 1991, Proc. Natl. Acad. Sci. U.S.A. 88:1138–1142). However, because VIM-2-positive, SLe$^x$-negative CHO cells showed no E-selectin-dependent adhesion (Lowe et al., 1991, J. Biol. Chem. 266:17467–17477; Walz et al., 1990, Science 250:1132–1135), VIM-2 epitope is not likely involved in such adhesion. A possibility for the VIM-2 antigen as a potential E-selectin ligand was denied by the fact that VIM-2 antibodies were unable to block adhesion and cells containing the VIM-2 antigen but not the SLe$^x$ structures were unable to bind to recombinant E-selectin and to activated endothelial cells (Lowe et al., 1991, J. Biol. Chem. 266:17467–17477; Walz et al., 1990, Science 250:1132–1135). In fact, ganglioside Str. 4 and 6, which have VIM-2 epitopes do not show appreciable adhesion under static conditions.

We now introduce a new assay based on interaction between latex beads coated with gangliosides and fluorescent beads coated with E- or P-selectin-Ig fusion protein. The interaction can be monitored easily by flow cytometry with appropriate gating. Using this assay, mixture of Fr. 10-1 and 10-2 (containing Str. 4 and 5), Fr. 13-1 (containing mainly Str. 7), and Fr. 14 (containing Str. 9 and 11 as major components) were found to bind strongly to E-selectin. Of particular importance is the observation that a mixture of different types of myelorollin greatly enhanced the rolling followed by adhesion. This is clearly demonstrated, not only by the flow cytometric method but also by cell adhesion in a dynamic flow chamber (see Table 2).

TABLE 2

| Number of E-selectin expressing cells adhered on myelorollin under dynamic flow (0.6 to 1.2 dynes/cm$^2$) | | |
|---|---|---|
| | 5 | 10 |
| Str. 6 (ACFH 18 antigen) | 5 (±2) | 3 (±1) |
| Fr. 14 (mixture of Str. 9, 10, 11, and 12) | 18 (±8) | 15 (±8) |

To summarize, Str. 1 and 2 (which have no internal fucosylation) showed no binding whatsoever to E-selectin coated surfaces. Among these fractions, only Fr. 13-1 contained a trace quantity of Str. 8 (which has SLe$^x$ determinant at the terminus, but also internal fucosylation). None of the other E-selectin-binding fractions contained SLe$^x$ epitope. Str. 3 (abundantly present in human solid cancers such as colonic, gastric, and lung carcinomas), having SLe$^x$ and internal fucosylation, bound to E-selectin coated surfaces.

Monosialogangliosides having terminally α2→3 sialylated and internally α1→3 fucosylated PLAs are the major components of neutrophils and myelogenous leukemia cells, and are collectively termed "myelorollin." mAbs FH6 (Fukushi et al., 1984, J. Biol. Chem. 259:10511–10517), CSLEX (Fukushima et al., 1984, Cancer Res. 44:5279–5285), and SNH3 and SNH4 (Muroi et al., 1992, Blood 79:713–719), previously identified as being directed to SLe$^x$ determinant, were found to react with all myelorollins. There is no mAb specific to SLe$^x$, i.e., not cross-reacting with any myelorollin. The specificity of these mAbs is under investigation.

We compared rolling and adhesion of E- and P-selectin-expressing CHO cells to ganglioside-coated latex beads affixed to microscopic slides under dynamic flow and static conditions. Only myelorollin (in the mixture of Fr. 10-1 and Fr. 10-2, Fr. 13-1 or Fr. 14), produced rolling of cells followed by adhesion under dynamic flow conditions. Fr. 10 and 14, which consist only of myelorollin with no trace of SLe$^x$, showed the strongest rolling and adhesion effects, particularly at 0.6 to 2.4 dynes/cm$^2$ shear stress. Str. 3, which has SLe$^x$ epitope with internal fucosylation, produced a lower level of adhesion and no cell rolling. Under static conditions, in contrast, Str. 3 caused much higher adhesion than myelorollin.

Since cell adhesion following rolling (rolling followed by adhesion) is regarded as a characteristic feature of selectin-dependent rolling and adhesion, we assume that myelorollin, as exemplified by Str. 4, 5, 7 10, 11, etc., plays a major role in adhesion of leukocytes, mediated by selectin expression on ECs. This conclusion is based on the is facts that: (i) Myelorollin is the major structure present in leukocytes and HL60 cells. (ii) only myelorollin (not SLe$^x$ with or without internal fucosylation) produces cell rolling followed by adhesion. (iii) SLe$^x$ without internal fucosylation is completely absent from neutrophils and HL60 cells.

In our study, under static conditions only fractions with terminal α2→3 sialylation and multiple internal α1→3 polyfucosylation (e.g., Structures C and D above, or a mixture of these structures) showed clear E-selectin binding upon application of TLC overlay technique with $^{32}$P-labeled CHO cells permanently expressing E- or P-selectin. Poly-LacNAc with terminal α2→3 sialylation and internal α1→3 monofucosylation (e.g., Structures A and B) did not show E-selectin binding under these conditions. These binding properties were confirmed in a static adhesion assay system using E-selectin expressing CHO cells overlaid on glycolipids coated on polystyrene beads affixed to glass plates. Glycolipid with typical SLe$^x$ structure (SLe$^x$-Le$^x$; VI$^3$NeuAcV$^3$FucIII$^3$FucnLc$_6$Cer) showed highest adhesion in the static system. By contrast, in a dynamic flow system using the same glycolipid-coated beads affixed to glass plates, SLe$^x$-Le$^x$ produced no rolling and only weak adhesion compared to Fr. 10-1, 10-2, 13-1 and 14. Strong rolling and adhesion of cells were observed when structures X and Y were used. Typical examples are Fr. 10-1, 10-2, Fr. 13-1 and Fr. 14 (mixture of structures A, B, C and D) also produced strong rolling and adhesion under physiological shear stress conditions.

Given the finding that a mixture of myelorollin structures (e.g., Fr. 14) produces the strongest rolling and adhesion under physiological shear stress conditions, we closely investigated Fr. 10-1, Fr. 10-2 and a mixture of equal quantities of Fr. 10-1 and 10-2. Rolling and adhesion caused by 100 ng of pure Fr. 10-1 and Fr. 10-2 under physiological shear stress were comparable to each other. Interestingly, a mixture of 50 ng each of these two components produced much higher rolling and adhesion, particularly under physiological shear stress. This trend was more evident when much smaller quantities of glycolipids were applied. The most dramatic enhancement was seen when 0.05 ng each of Fr. 10-1 and 10-2 were used, compared to 0.1 ng of either component alone. These findings suggest that extremely small quantities of Fr. 10-1 and 10-2 may interact with each other to form a suitable structure for E-selectin causing rolling and adhesion under dynamic flow conditions. The mechanism for this synergistic effect remains unknown.

SLe$^x$-Le$^x$ structure, which produced the strongest E-selectin-dependent adhesion under static conditions, was weaker than myelorollin structures under dynamic flow conditions (compare FIG. 2A vs. FIGS. 2C, 2D and 2E). The difference was even more striking at very low concentration. SLe$^x$-Le$^x$ at a concentration of 0.05 ng caused essentially no cell rolling and adhesion (FIG. 4A), whereas a mixture of Fr. 10-1 and 10-2 (0.05 ng each, giving the same molarity as 0.05 ng SLe$^x$-Le$^x$) caused strong rolling and adhesion (FIG. 4B). The enhancement by a mixture of Fr. 10-1 and 10-2 compared to either fraction alone was more pronounced when low (i.e., 0.05–0.1 ng) rather than high concentration (50–100 ng) was used. In contrast to the effects of Fr. 10-1 and 10-2, SLe$^x$-Le$^x$ at low concentration (i.e., 0.05–0.1 ng) did not cause any rolling or adhesion of E-selectin expressing cells.

These results indicate that myelorollin, rather than SLe$^x$-Le$^x$, is the major ligand for E-selectin-dependent rolling and adhesion of myeloid cells on vascular endothelial cells under physiological dynamic flow conditions.

Our results also suggest an explanation of why a series of poly-LacNAc structures with differing location of α1→3 fucosylation, and terminal sialylation, are present and form arrays on the neutrophil surface. Combinations of specific structures may form high-, middle-, or low-affinity binding sites in order to optimally bind E-selectin under high-, middle-, or low-shear stress dynamic flow conditions. Poly-LacNAc is known to form helical structures. Myelorollin and myeloglycan may have helical backbone structures onto which multiple or single fucosyl residues are linked and oriented in different directions. Such helical structures, based on the positioning of the fucosyl residues, could interact with each other.

Throughout this study, P-selectin-dependent binding was not observed with any of the gangliosides tested, by either flow cytometric methods as described above or by adhesion of P-selectin-expressing CHO cells to ganglioside-coated plates, either under static or dynamic flow conditions. P-selectin-dependent adhesion clearly requires a "PSGL-1-like" assembler molecule in addition to specific carbohydrate structure (Handa et al., 1995, Int. J. Oncol. 6:773–781; Sako et al., 1993, Cell 75: 1179–1186). Further studies on the carbohydrate epitope required for P-selectin binding are in progress.

Three possible schemes for assembly of sialic acid (SA) and fucosyl residue (Fuc) on polylactosamine chain of myelorollin are shown in FIG. 7. Repetitive Galβ1→4GlcNAcβ1→3Galβ1→4GlcNAcβ1→3Gal forms a helical structure (Atkins et al., Polymer 15:263–271, 1974; Rees DA, MTP Intl Review of Science 5:1–42, 1975; Niemann et al., Biochem Biophys Res Commun 81:1286–1293, 1978). There is a high possibility that double or triple helical structure is formed through hydrogen bonding (Rees DA, MTP Intl Review of Science 5:1–42, 1975; Frey-Wyssling A., *Submicroscopic morphology of protoplasm*, Elsevier Publ. Co., Amsterdam, 1953). Scheme A is a possible double helical association of two myelorollin molecules having a single Fuc at different internal GlcNAc residues (locations designated as 1 and 2; Fuc residues designated at "Fuc 1" and "Fuc 2") (FIG. 7, panel A). Scheme B: possible double helical association of two identical myelorollin molecules each having two Fuc residues; one each at locations 1 and 2; residues designated "Fuc 1" and "Fuc 2" as above (FIG. 7, panel B). Scheme C is the configuration of SLe$^x$ having Fuc "x" at the penultimate GlcNAc (FIG. 7, panel C).

Rolling/adhesion of E-selectin expressing cells under dynamic conditions is presumably controlled by spatial configuration and interrelationship of SA and Fuc: their angle distance, and orientation along helical polylactosamine backbone.

A possible configuration and interrelationship between SA and Fuc viewed along the axis of the helical backbone is shown in panel D of FIG. 7 (I corresponds to Scheme A; II to Scheme B; III to Scheme C). Configuration I, formed between two myelorollin molecules having different Fuc locations (Fuc 1[black] and Fuc 2 [white]) may greatly enhance rolling and adhesion abilities, as exemplified by the mixture of Fr. 10-1 and 10-2. Perhaps Fuc 1 and Fuc 2 are located at symmetrical positions along the helical polylactosamine backbone as shown.

Rolling/adhesion ability between myelorollin molecules associated as in Scheme B and viewed along the axis as in II is nearly the same as for two molecules associated as in Scheme A. Perhaps Fuc 1 and Fuc 2 on the two molecules are located at symmetrical positions as shown in II.

SLe$^x$ may have a very different configuration (Scheme C; view III), and fail to cause rolling.

While the preferred embodiment of the invention has been illustrated and described, it will be appreciated that various changes can be made therein without departing from the spirit and scope of the invention.

Various publications are cited herein, the disclosures of which are incorporated by reference in their entireties.

What is claimed is:

1. A polylactosamine having the formula:

Galβ4GlcNAcβ3Galβ4GlcNAcβ3Galβ4GlcNAcβ→R
            3                                          3
NeuAcα                               Fucα wherein R is:
—H;
a substituted or unsubstituted aryl group;
an alkyl, alkenyl or hydroxyalkyl group having 1 to 10 carbon atoms;
a lipid;
an oligosaccharide;
a pharmaceutically active ingredient; or
a solid carrier.

2. The polylactosamine of claim 1, in which R is a pharmaceutically active ingredient, wherein said pharmaceutically active ingredient is a non-steroid anti-inflammatory drug.

3. The polylactosamine of claim 1, in which R is a lipid, wherein said lipid is a ceramide.

4. A composition comprising:
(a) a first polylactosamine having the formula:

Galβ4GlcNAcβ3Galβ4GlcNAcβ3Galβ4GlcNAcβ→R
            3                                          3
NeuAcα                               Fucα and
(b) a second polylactosamine having the formula:

Galβ4GlcNAcβ3Galβ4GlcNAcβ3Galβ4GlcNAcβ→R
            3                                          3
NeuAcα                               Fucα wherein R is:
—H;
a substituted or unsubstituted aryl group;
an alkyl, alkenyl or hydroxyalkyl group having 1 to 10 carbon atoms;
a lipid;
an oligosaccharide;
a pharmaceutically active ingredient; or
a solid carrier.

5. The composition of claim 4, in which R is a pharmaceutically active ingredient, wherein said pharmaceutically active ingredient is a non-steroid anti-inflammatory drug.

6. The composition of claim 4, in which R is a lipid, wherein said lipid is a ceramide.

7. A composition which comprises:
(a) a first polylactosamine having the formula:

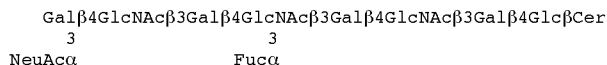

and (b) a second polylactosamine having the formula:

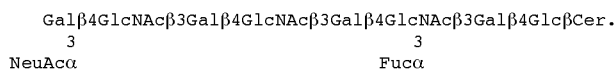

8. A composition which comprises:
(a) a first polylactosamine having the formula:

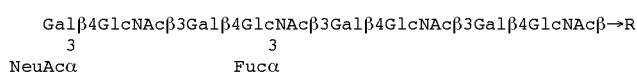

(b) a second polylactosamine having the formula:

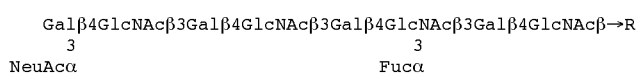

(c) a third polylactosamine having the formula:

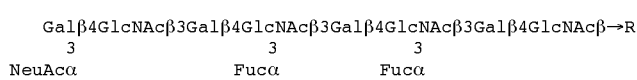

and (d) a fourth polylactosamine having the formula:

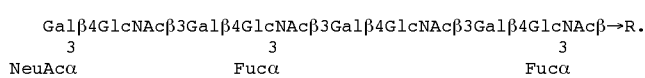

9. A composition which comprises:
(a) a first polylactosamine having the formula:

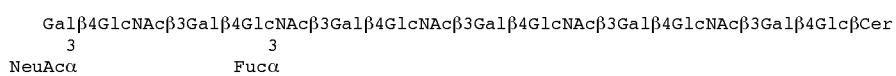

(b) a second polylactosamine having the formula:

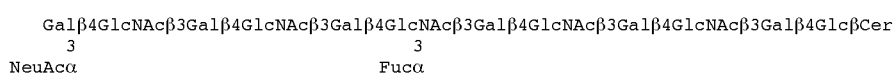

(c) a third polylactosamine having the formula:

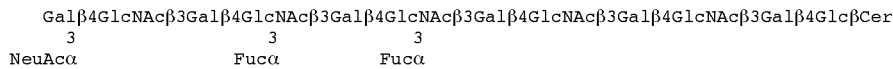

and (d) a fourth polylactosamine having the formula:

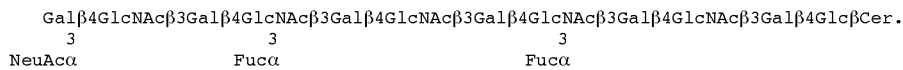

10. A composition comprising:

(a) first polylactosamine having the formula:

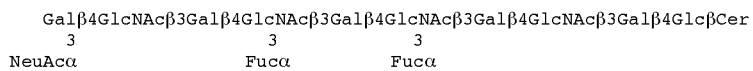

and (b) a second polylactosamine having the formula:

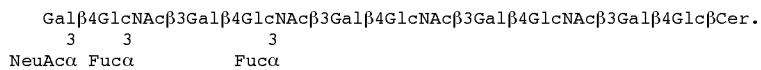

11. A pharmaceutical composition which comprises the composition as in any of claims 4, 5 or 6–10, and a pharmaceutically acceptable carrier.

12. A method for inhibiting E-selectin-dependent rolling of a first cell on a second cell, comprising exposing the first cell and/or the second cell to an inhibitory amount of the composition as in any of claims 4, 5 or 6–10, wherein the cell expresses a ligand that causes E-selectin-dependent cell rolling, and the second cell expresses E-selectin.

13. The method according to claim 12, wherein the E-selectin-dependent rolling of a first cell on a second cell is inhibited in vitro.

14. A method for treating inflammation, comprising administering to a patient a therapeutically effective dose of the pharmaceutical composition of claim 11.

15. A polylactosamine, which has the formula:

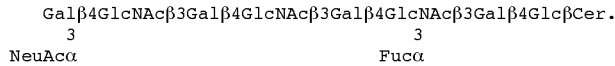

16. A polylactosamine having the formula:

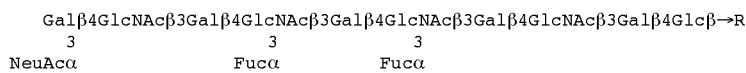

wherein R is:
—H;
a substituted or unsubstituted aryl group;
an alkyl, alkenyl or hydroxyalkyl group having 1 to 10 carbon atoms;
a lipid;
an oligosaccharide;
a pharmaceutically active ingredient; or
a solid carrier.

17. The polylactosamine of claim 16, in which R is a pharmaceutically active ingredient, wherein said pharmaceutically active ingredient is a non-steroid anti-inflammatory drug.

18. The polylactosamine of claim 16, in which R is a lipid, wherein said lipid is a ceramide.

19. A pharmaceutical composition which comprises the polylactosamine as in any of claims 1, 2, 3, 15, 16, 17 or 18, and a pharmaceutically acceptable carrier.

20. A method for inhibiting E-selectin-dependent rolling of a first cell on a second cell, comprising exposing the first cell and/or the second cell to an inhibitory amount of the polylactosamine as in any of claims 1, 2, 3, 15, 16, 17 or 18, wherein the first cell expresses a ligand that causes E-selectin-dependent cell rolling, and the second cell expresses E-selectin.

21. A method for treating inflammation, comprising administering to a patient a therapeutically effective dose of the pharmaceutical composition of claim 19.

22. The method according to claim 20, wherein the E-selectin-dependent rolling of a first cell on a second cell is inhibited in vitro.

* * * * *